(12) United States Patent
Vermeulen et al.

(10) Patent No.: US 8,334,352 B2
(45) Date of Patent: Dec. 18, 2012

(54) BRANCHED POLYESTERAMINE ACRYLATE

(75) Inventors: Jacobus Adriaan Antonius Vermeulen, Born (NL); Alfred Jean Paul Buckmann, Waalwijk (NL); Rudolfus Antonius Theodorus Maria Benthem, Limbricht (NL); Emilio Martin Bouwens, Hendrik Ido Ambacht (NL); Stijn Witters, Lommel (BE)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 12/678,571

(22) PCT Filed: Sep. 19, 2008

(86) PCT No.: PCT/EP2008/062554
§ 371 (c)(1),
(2), (4) Date: Sep. 14, 2010

(87) PCT Pub. No.: WO2009/037345
PCT Pub. Date: Mar. 26, 2009

(65) Prior Publication Data
US 2011/0003908 A1 Jan. 6, 2011

(30) Foreign Application Priority Data
Sep. 21, 2007 (EP) .................................... 07018539

(51) Int. Cl.
*C08F 26/00* (2006.01)
*C08F 8/30* (2006.01)
*C08F 8/00* (2006.01)
*C08J 3/28* (2006.01)

(52) U.S. Cl. ........... 526/312; 522/152; 524/555; 525/55

(58) Field of Classification Search .................. 522/152; 526/312; 524/555; 525/55
See application file for complete search history.

(56) References Cited

FOREIGN PATENT DOCUMENTS

| DE | 42 25 921 | 2/1994 |
|---|---|---|
| EP | 0 280 222 | 8/1988 |
| WO | 2004/087790 | 10/2004 |
| WO | 2004/108795 | 12/2004 |

OTHER PUBLICATIONS

Yaowu Sha (Sha et al., "A Divergent Synthesis of new Aliphatic Poly(ester-amine) Dendrimers Bearing Periphera Hydroxyl or Acryiate Groups", Tetrahedron Letters, Elsevier, Amsterdam, vot. 43, No. 51, Dec. 16, 2002, pp. 9417-9419).*

Written Opinion of the International Searching Authority for PCT/EP2008/062554, mailed Jan. 29, 2009.

Sha et al., "A Divergent Synthesis of new Aliphatic Poly(ester-amine) Dendrimers Bearing Periphera Hydroxyl or Acrylate Groups", Tetrahedron Letters, Elsevier, Amsterdam, vol. 43, No. 51, Dec. 16, 2002, pp. 9417-9419, XP004392989.

Schobert at al., "Conjugates of Methyl 6-aminopenicillanate with Biscatechol-Hydroxamate Chelators: synthesis and Siderophoric Activity", Tetrahedron, Elsevier Science Publishers, Amsterdam, NL, vol. 62, No. 33, Aug. 14, 2006, pp. 7799-7808, XP005534748.

* cited by examiner

*Primary Examiner* — William Cheung
(74) *Attorney, Agent, or Firm* — Nixon & Vanderhye P.C.

(57) ABSTRACT

The present invention relates to a method for preparing a branched non dendrimeric macromolecule, comprising: a) providing an addition product of an α,β-olefinically unsaturated compound and an amine comprising at least two hydroxyl groups; and b) esterifying at least part of the hydroxyl groups of the addition product with an olefinically unsaturated carboxylic acid, an olefinically unsaturated carboxylate anion or an olefinically unsaturated carboxylic acid anhydride. The invention further relates to macromolecules obtainable by a method of the invention.

26 Claims, No Drawings

BRANCHED POLYESTERAMINE ACRYLATE

This application is the U.S. national phase of International Application No. PCT/EP2008/062554, filed 19 Sep. 2008, which designated the U.S. and claims priority to European Application No. 07018539.2, filed 21 Sep. 2007, the entire contents of each of which are hereby incorporated by reference.

The invention relates to a method for preparing macromolecule(s), to macromolecule(s) obtainable by such method, to composition(s) comprising such a macromolecule(s), and to the use of such macromolecule(s).

Macromolecule(s) of the invention may be compounds and/or polymers and although they may also be branched it is preferred that they are not dendrimers (which are globular repeatedly branched, monodisperse, highly ordered symmetric macromolecules containing a single chemically addressable group called a focal point).

Acrylate and methacrylate functional materials may be cured by radiation and are widely used in many applications, such as coatings, inks, varnishes, adhesives, sealants, elastomers, crosslinked films, foundry sand binders and/or composite structures. Although these materials generally have good properties for such applications, as they are highly viscous liquids, usually they need to be diluted with a relatively high amount of reactive diluent to lower their viscosity sufficiently (typically to <10 Pa·s, or even <2 Pa·s) to have the high flowability that is also required.

Reactive diluents are typically irritants and must be labelled as such, which is both off putting to the end user and also may restrict how the final product can be used. Additionally, any unreacted diluents left in a composition after curing will migrate to the surface as they are low molecular weight components. This is highly undesirable for many end uses such as coatings designed to contact food, where only high molecular weight components of low mobility are likely to be approved by regulators.

Ethoxylated and propoxylated reactive diluents have been used to address these problems, these are expensive and/or have a relatively low thinning capacity, so must be used in large amounts.

If organic solvents (e.g. acetone, dimethylketone) are used to dilute the composition, then volatile organic compounds (VOC) will be released on drying. This may cause irritation to people exposed to the vapour and/or affect a property of the dried resin.

Although water is a cheap and safe diluent, as typical radiation curable resins are poorly soluble in water, large quantities of water are needed to significantly reduce viscosity. To dry such aqueous compositions effectively, both IR and UV radiation may be needed and this is unacceptable for many applications, such as graphic arts. The presence of large amounts of aqueous diluent can also adversely affect the properties of the cured composition by for example increasing its susceptibility to and/or penetration by water.

In general it is desirable to formulate with low concentrations of diluents otherwise the formulation can shrink too much on curing, especially where fast curing multifunctional monomers are used.

Traditionally, acrylate resins are cured by free radical chain mechanisms where an initiator is added that forms radicals when it is heated or irradiated. However radical curing can also produce migratable fragments, which may have undesirable effects on the environment or be detrimental to health. Radical curing may also be inhibited by the presence of oxygen.

Various references describe compounds and oligomers obtained from Michael addition of multi-functional acrylates and hydroxyl functional amines. Some of these are described below.

'Water-soluble degradable hyperbranched polyesters: novel candidates for drug delivery?' Biomacromolecules 2003, 4, 704-712, Gao et al describes hyperbranched polyesters that contain a large number of terminal hydroxyl groups. Such polyesters may be prepared by a Michael reaction between diethanol amine and methyl acrylate. This article teaches away from further reacting the hydroxyl groups in the resultant polyester (e.g. in a subsequent esterfication step) as they are designed to be water soluble. There would be no reason for a reader to add further acrylate functional groups to these polyesters as they are designed to aid drug delivery and are not intended to form curable coatings.

EP 280222 (BASF) describes radiation curable addition products that are esters made from (meth)acrylic acid and a polyol with a primary mono amine. These products have a very different structure from the branched macromolecules of the present invention. The amine is added in small amounts (amine to ester ratio is from 0.05:1 to 0.4:1) so the reaction between them is not substantially complete. A reader would have no reason to increase the amount of amine which would remove radiation curable acrylate groups from the adduct. There is also no teaching to subsequently esterify hydroxy groups on the amine acrylate adduct. The product described in this document may be liquid or solid at room temperature, is used in coatings or inks, is said to be storage-stable, and cures quickly even in the presence of air. On curing these resins shrink to a relatively high degree, especially if used undiluted. Also, they require high energies to cure satisfactorily which results either in a high concentration of migratable species in the cured resin or a low cure speed.

EP 297344 (PPG) describes an ungelled coating composition that comprises a hydroxy functional Michael adduct formed by reacting a primary or secondary amine and an acrylate. The adduct is then mixed with a curing agent such as a diacrylate capable of cross-linking the hydroxyl groups during thermal curing to form a polymeric coating. This is different from the present invention in which a low molecular weight branched macromolecule is formed by first reacting an acrylate with a polyol amine and then esterfying the product with an acrylic acid.

EP 586849 (=U.S. Pat. No. 5,482,649) (Bayer) describes preparing a radiation curable amino acrylate by adding a viscous primary mono- or diamine, an ester of acrylic acid and an ether alcohol. These products have a very different structure from the branched macromolecules of the present invention. The amine is added in small amounts (amine to ester ratio is from 0.05:1 to 0.25:1). These resins also exhibit high shrink when cured, especially when undiluted and require high energies to cure satisfactorily.

US 2002-0151638 (Bayer) describes a hydroxy functional water dispersible acrylate copolymer suitable for use as a binder in paint. The copolymer may be prepared from hydroxy functional monomers. The Examples of Bayer teach that small amounts of polyhydroxyl functional amine synergist (such as diethanol amine, DEA) may be added to the monomer mixture during preparation of the dispersion. The amine synergist is not present in sufficient amounts to react with a large proportion of the acrylate groups and Bayer does not then teach subsequent esterification of the hydroxyl groups in the resultant product. Macromolecules of the present invention are preferably used as reactive diluents for radiation curable compositions which is very different from the end use for the copolymers described in this reference.

US 2003-0069352 (BASF) also describes aqueous (meth) acrylate copolymer dispersions prepared from hydroxyl functional monomers including acrylates. BASF teaches that hydroxy functional amines may be used as neutralising agents during preparation of these polymers. These copolymers are very different from the branched macromolecules described herein.

US 2003-0073757 (Ashland) describes self-photo initiating oligomers that comprise tertiary amine groups obtained from Michael addition of a multi-functional acrylate a Michael donor to from a product which then reacts with a primary or secondary amine (which may be a hydroxylamine) to form the oligomer. The acrylate is used in excess of the Michael donor and the final oligomer contains large amounts of unreacted acrylate groups (the acrylate to amine groups in a ratio from 100:1 to 2:1).

This is in contrast to the present invention where for example acrylate(s) are reacted with (hydroxy functional) amine(s) substantially to completion to form a product which has few or no acrylate groups thereon and so is not readily cured by radiation. The hydroxyl functional product is then esterified to form the acrylate functional macromolecules of the invention which have different properties (for example are much more highly branched) than the oligomers described in '757 Ashland.

US 2005-0261388 (Ashland) describes liquid un-crosslinked UV curable resins prepared by Michael addition of Michael acceptors (such as acrylates) and Michael donors (such as beta di-carbonyl compounds). Ashland teaches that such adducts can optionally further react with amines synergists (including hydroxy amines). However there is no teaching that the reaction with the amines should be continued substantially to completion (i.e. reacting all acrylate groups) or that then the hydroxyl groups on this product should be esterified. Indeed as Ashland teaches that the resins are UV curable the reader would be deterred from using large amounts of amine to react more than a small fraction of the acrylate groups. US 2005-0261391 (Ashland) describes the use of the resins described in '188 in over print varnishes.

WO 2004-101624 (BASF) describes a method of producing hyperbanched polyurethanes by reacting poly-isocyanates with a hydroxy functional amine intermediate formed by reacting hydroxy amines with acrylates. These amine intermediates are not esterified and this reference is not relevant to the macromolecules of the present invention.

WO 2005-108434, WO 2005-111105 and WO 2005-111130 (all Ashland) describe various multi-functional acrylate resins formed by a Michael addition of acrylates with beta dicarbonyl compounds (such as beta keto esters or amides). These references teach (e.g. Example 3 of '105) that secondary amine may be blended with such resins (with the resin in excess) to form a UV curable composition. The amine is mixed as an additive with the acrylate rather than reacted with it and these documents do not suggest a subsequent esterification step.

Many documents (such as WO 2005-028432; US 2007-244296; US 2007-073004; U.S. Pat. No. 4,871,779; U.S. Pat. No. 4,857,599; U.S. Pat. No. 4,694,064; U.S. Pat. No. 4,568,737; U.S. Pat. No. 4,558,120; U.S. Pat. No. 4,507,466; U.S. Pat. No. 4,435,548; EP 556871; EP 234408; EP 066366; Tetrahedron Letters 43 (2002) 9417-9419; Macomol. Chem. Phys. 197, 621-631 (1996)) also describe the preparation of various monodisperse dendrimers (typically for use in drug delivery) that may be prepared using Michael addition of acrylates. These are not relevant to the macromolecules of the present invention which are not dendrimers.

None of these prior art documents teach the macromolecules of the present invention as for example none suggest esterifying hydroxy functional amine-acrylate non-dendrimeric adducts and for the reasons given above there would be no reason for a reader of any of these documents to consider doing so.

It is an object of the present invention to provide novel method(s) for preparing macromolecule(s) such as those based upon acrylates, methacrylate or other esters comprising a polyolefinically unsaturated moieties.

It is a further object to provide novel macromolecule(s) which can be used as an replacement for, alternative to and/or in addition to known acrylates and which may be suitable for preparing coating compositions such as coatings, inks, adhesives, varnishes and/or paints.

It is a further object to provide liquid macromolecule(s) compositions (suitable for use in application(s) where acrylate resin(s) can be used) having a relatively low viscosity.

It is a further object to provide water-dilutable macromolecule(s) (suitable for use in an application(s) where acrylate resin(s) can be used).

It is a further object to provide curable macromolecule(s) (suitable for use in application(s) where acrylate resin(s) can be used), that adhere well to suitable substrate material(s), preferably to a variety of different materials, such as one or more of: polymeric materials, metals, ceramics, glass, wood, textile and/or paper.

It is a particular object to provide curable macromolecule(s) (suitable for use in application(s) where acrylate resin(s) can be used) that can be cured quickly (having a high reactivity), preferably by photo-curing, that have a low viscosity before curing, that display low shrink upon curing (of the resultant cured material compared to the uncured compound), and/or comprise a low amount of migratable species after curing.

Another object of the present invention is to address one or more of the problems mentioned herein. Object(s) that may be realised in accordance with the invention will be apparent from the remainder of the description and/or the claims.

It has been found that one or more of the objects identified herein are achieved by forming the product of an olefinically unsaturated compound and an amine comprising at least two hydroxyl groups and then modifying the hydroxy groups of the adduct in a specific way.

Accordingly, the present invention relates to a method comprising a) providing an addition product of an $\alpha,\beta$-olefinically unsaturated compound and an amine comprising at least two hydroxy groups; and b) esterifying at least part, preferably a substantial part, of the hydroxyl groups of the addition product (originating from the amine) with an olefinically unsaturated carboxylic compound, Preferably the olefinically unsaturated carboxylic compound used in step (b) is selected from the group consisting of one or more of: olefinically unsaturated carboxylic acid(s), olefinically unsaturated carboxylate anion(s), olefinically unsaturated carboxylic acid anhydride(s), ester(s) of olefinically unsaturated carboxylic acid(s), olefinically unsaturated acid halogenide(s) and/or any suitable mixtures thereof; more preferably from olefinically unsaturated: carboxylic acid(s), carboxylate anion(s), carboxylic acid anhydride(s), and/or carboxylic ester(s), most preferably from $\alpha,\beta$-olefinically unsaturated carboxylic acid(s) and/or esters thereof, conveniently $\alpha,\beta$-olefinically unsaturated $C_{3-50}$-carboxylic acid(s) and/or $\alpha,\beta$ olefinically unsaturated $C_{4-50}$-carboxylic ester(s), more conveniently $\alpha,\beta$ olefinically unsaturated $C_{4-50}$carboxylic (poly)acid(s) and/or α,β olefinically unsaturated α,β $C_{6-50}$carboxylic (poly)ester(s), most conveniently α,β olefinically unsaturated $C_{4-50}$carboxylic (di, tri or tetra)acid(s) and/or α,β olefinically unsaturated α,β $C_{4-50}$carboxylic (di, tri or tetra)ester(s), for example α,β olefinically unsaturated $C_{4-30}$carboxylic di-acid(s) and/or di-esters such as $C_{4-20}$di-(meth)acrylates.

Unless the context herein indicates otherwise the term 'carboxylic acid' as used herein encompasses anhydrides thereof, corresponding carboxylate anion(s) of the acid, esters of the acid and acid halogenides of the acid. An acid halogenide is a compound comprising a —(C=O)Hal group wherein Hal is a halogen atom, preferably chlorine.

The term 'substantial part of' as used herein (and similar terms such as 'substantially all' and 'substantially complete') mean from about 80% to 100%, preferably from about 90% to 100%, more preferably from about 95% to 100%.

The term "esterifying" as used herein is denotes esterification of an hydroxyl group with any compound of which the reaction product is an ester. Thus, it includes reaction with a carboxylic acid, with a conjugated base of the carboxylic acid, with an anhydride of the carboxylic acid esterification with an ester of the carboxylic acid and esterification with an acid halogenide. Esterification with an ester is also known as trans-esterification. Usually, the esterification is carried out to the extent that—on average—the number of olefinic unsaturations in the molecules of the product resulting from reaction b) is equal to or larger than the number of olefinic unsaturations in the α,β-olefinically unsaturated compound before reaction with the amine. A residue or part of the macromolecule product of reaction b) is formed from the α,β-olefinically unsaturated compound used in step a). This residue may be conveniently referred to herein as a core molecule or the core of the macromolecule.

A used herein the term 'macromolecule' refers both to one or more compounds of large molecular weight made for example directly by organic synthesis (in one or more steps) and also to polymers prepared by polymerisation process, the polymers comprising a mixture of macromolecules of different number of repeat units and/or molecular weights (where the polymer has a polydispersity of greater than one). Macromolecules of the invention may be compounds and/or polymers and although they are branched they are not dendrimers (which are globular repeatedly branched, monodisperse, highly ordered symmetric macromolecules containing a single chemically addressable group called a focal point). Preferred macromolecules of the invention are polymeric that is have a polydispersity of >1. Polymers must be distinguished from mixtures of macromolecules, for example a mixture of one or more (monodisperse) dendrimers blended together is non-stochastic and is very different from the distribution of individual macromolecules present in a polymer.

The invention further relates to a branched macromolecule obtainable by a method according to any of the preceding claims. A branched macromolecule, is a molecule comprising at least one nitrogen to which at least three moieties selected from the group of organic moieties (including organo silicon moieties) and silicate moieties are attached. Each such moiety attached to a trivalent (or tervalent if the nitrogen is positively charged) nitrogen can be considered a branch. In particular a branched molecule may comprise at least one nitrogen to which three or four carbons are attached. More in particular, the term "branched" is used herein to indicate that a tertiary amine or quaternary ammonium cation is present in the molecule, wherein the organic groups attached to the nitrogen comprise an ester moiety.

The term "hyperbranched" is known in the art. The classic approach to hyperbranched polymers is the polycondensation of $AB_n$ type monomers (wherein n is at least 2), as described by Flory (Principles of Polymer Chemistry, Cornell University Press, Ithaca, N.Y., 1953). A and B stand for independent functional groups which (under the conditions of the reaction) are only reactive with one another and not amongst themselves. Polycondensation of this monomer type will lead to highly branched tree-like structures. Alternative approaches of forming hyperbranched molecules are described in R.A.T.M. van Benthem, Progress in Organic Coatings 40 (2000), 203-214, see in particular the introduction, FIGS. 1 and 2 and the explanation thereof; and in Chao Gao et al. Biomacromolecules 2003, 4, 704-712, see in particular page 705 last paragraph until page 6, first full paragraph of the right hand column, Scheme 1 and Scheme 2. Chao also teaches that at least two types of monomers can be used to build the hyperbranched structure. The contents of these publications that relate to hyperbranched structures are incorporated herein by reference.

The "hyperbranched molecule" is in particular used in accordance with the invention, for a branched molecule wherein at least one of the branches is further branched. For example at least one branch, preferably at least two branches may comprise at least one further nitrogen to which two or three additional organic moieties, usually organic moieties comprising an ester, are attached. Generally hyperbranched molecules of the invention comprise at least two nitrogens which are part of one or more tertiary amine(s) and/or quaternary ammonium cation(s) moieties and preferably at least three, more preferably at least four such nitrogen containing moieties (N-moieties) may be present. There is no particular upper limit on the number of such N-moieties in macromolecules of the invention, but depending upon the desired viscosity (also related to molecular weight) and/or number of functional groups per molecule usefully the number of N-moieties is $\leq 20$, more usefully $\leq 16$, most usefully $\leq 10$, in particular $\leq 8$, for example $\leq 6$.

Macromolecule(s) of the invention may be compounds and/or polymers and although they may also be branched it is preferred that they are not dendrimers which are globular, monodisperse macromolecules. Macromolecules of the invention usefully comprise polymers (i.e. polydisperse mixtures), non dendrimeric single compounds and/or mixtures thereof. It is possible in one embodiment of the invention to provide compositions (such as coatings, adhesives, inks and/or reactive diluents) that also comprises dendrimers. Such dendrimers may be prepared in a similar manner to the macromolecules described herein (e.g. Michael addition of hydroxy amine and acrylate to form a hydroxy adduct followed by esterification of the hydroxy adduct with more acrylate to form an acrylate functional product and repetition of both steps over several generations).

Dendrimers have the disadvantage that they are prepared by laborious multi step self condensation processes where the same functionalities react in multiple generation steps. Exact control of the process conditions may be needed to prevent side reactions and the resultant dendrimer is a very bulky macromolecule. One advantage of certain non-dendrimeric macromolecules of the present invention is that they are easy to prepare and can be made in a few steps. Preferred macromolecules are those obtained from steps (a) and (b) performed once. However as the product from (b) can react again in step (a) it is possible to repeat both steps a few more times to produce larger macromolecules. If steps (a) and (b) are repeated, it is possible to use different reagents independently in each repeated step (unlike dendrimers prepared by multi-generation self condensations). Non-dendrimer macromolecules of the present invention may generally be cheaper to produce than dendrimers of similar functionality yet surprisingly still provide improved properties. For these reasons amongst others it is therefore preferred that macromolecules of the invention are not dendrimers.

As used herein 'radiation-curable' denotes a material which will polymerize when irradiated for example with actinic radiation and/or ultraviolet (UV) light (optionally in the presence of another ingredient such as a photo-initiator) and/or ionizing radiation (such as electron-beam). Actinic radiation is electromagnetic radiation capable of producing photochemical action, but of insufficient energy to produce ions in commonly used materials, and usually has a wavelength of greater than 185 nanometres. UV light is radiant energy having a wavelength from 180 to 400 nanometres (1.8 to $4.0 \times 10^{-7}$ meters). Ionizing radiation is particle or electromagnetic energy capable of producing ions in common materials; usually energies of greater than about 10 electron volts or $16 \times 10^{-19}$ joules. Electron beam (e-beam) is a beam of electrons typically displaced from a metallic filament by a high voltage source of acceleration. Preferred methods to achieve radiation polymerization comprise UV light and/or e-beam. The polymerization mechanism can be any suitable method that can be induced by radiation (e.g. free radical, cationic etc).

Surprisingly, it has been found possible in an advantageous embodiment of the invention to provide a liquid macromolecule, suitable for use in an application wherein an acrylate resin can be used, having a relatively low viscosity, which is water-dilutable and shows good curing properties.

It has been that certain macromolecules of the invention (suitable for use in applications where acrylate and similar resins are used) can adhere well to a wide variety of suitable substrates whether on their own, or added to a composition to improve its adhesion. Suitable substrates may be selected from one or more of: polymeric materials, metals, ceramics, glass, wood, textile and paper. In particular macromolecules of the invention adhere particularly well to polymeric substrates, such as those selected from the group consisting of: polyolefins (e.g. polypropylene, polyethylene and/or copolymers thereof) polyesters (e.g. polyethylene terephthalate, PET), and/or mixtures and copolymers thereof. It is surprising that macromolecules of the invention can improve adhesion to such a wide variety polymeric films and foils, whether non-stretched, oriented (e.g. bi-axially oriented), co-extruded and/or laminated with different plastics.

An advantageous embodiment of the invention provides a suitable liquid macromolecule that can be cured fast by photo-curing, that has a low viscosity before curing, and that displays low shrink and good adhesion upon curing.

A macromolecule that cures quickly is advantageous in applications where the composition of which it is a part (e.g. ink or adhesive) is applied very rapidly to the substrate in methods using sheet fed or sheet rotation techniques, off set printing, ink jet printing (e.g. to a high speed web) or the like. Rapid cure is desirably for a composition to be applied at high speed, whilst maintaining properties such as high printing quality (high resolution, low smear), low blocking etc.

Low viscosity macromolecules of the invention may be useful in formulating compositions where low viscosity is required, such as for ink jet printing or using a spray gun.

A macromolecule of the invention may further advantageously be used in combination with another curable material (e.g. compound, polymer or mixture). If the other material has a higher viscosity, the macromolecule of the invention may be a diluent (for example macromolecules of the invention may be used to dilute a curable epoxyacrylate).

Advantageously, macromolecules of the invention may be used as a substitute (in whole or in part) for low molecular weight monomers more conventionally used as reactive diluents in curable compositions. As indicated above, low molecular weight reactive diluents are disadvantageous for several reasons discussed above (they are irritants, have a low cure speed, uncured monomers may migrate to the surface of a coating, compositions with such diluents shrink significantly on curing). Therefore one embodiment of the invention provides a curable composition comprising macromolecules of the invention where the composition comprises <25% of low-molecular monomers by weight of the polymerisable components, preferably <10%, more preferably <5%, most preferably <1%, and for example is essentially free of low-molecular monomers (i.e. <0.5%). Low molecular weight monomers may be considered as those monomers that have a lower molecular mass that the lowest molecular mass (or $M_n$ if a polymer) given herein for the macromolecules of the invention (conveniently $\leq 200$ g/mol).

As used herein, the term "macromolecule" denotes a molecule having a large molecular mass, in particular a molecular mass of 200 g/mol or more, preferably 270 g/mol or more, more preferably 350 g/mol or more, and most preferably 400 g/mol or more. A relatively high molecular mass may be desirable for a particularly low shrink upon curing, conveniently at least 500 g/mol, more conveniently at least 750 g/mol, most conveniently at least 1000 g/mol. The macromolecule compound may be a single compound (for example prepared by an organic synthesis in one or more steps), a polymeric material (for example prepared by a suitable polymerisation method) comprising a mixture of compounds with different numbers of repeat units, a polymerisable macromolecular compound and/or any suitable mixtures thereof. If the macromolecule of the invention is polymeric (i.e. obtained by polymerisation and having a polydispersity of greater than 1) then the molecular mass values given herein will be a number average molecular mass ($M_n$) of such polymers of the invention.

Polymerisable macromolecules of the invention that are liquid may typically have a molecular mass of 100 kg/mol or less, although macromolecules of higher molecular mass may also be liquid, if for example they comprise a moiety (such as a polyethylene glycol, PEG) that reduces viscosity at a high molecular mass. Preferred macromolecules have a molecular mass of less than 50 kg/mol, more preferably less than 10 kg/mol, most preferably less than 5 kg/mol, for example less than 3 kg/mol. Advantageously macromolecules with such mass have lower viscosity and/or improved water resistance. Conveniently the macromolecule comprises hydrophilic polymeric moeit(ies), such as PEG.

As used herein, the term "polymer" denotes a structure that essentially comprises a multiple repetition of units derived, actually or conceptually, from molecules of relative low molecular mass. Such polymers may include crosslinked networks, branched polymers and linear polymers. Oligomers are considered a sub set of polymers, i.e. polymers having a relatively low number of repetitions of units derived, actually or conceptually, from molecules of low relative molecular mass. Generally in an oligomer adding or removing even one repeat unit from the oligomer has a significant effect on the properties of the resultant oligomer whereas a polymer is so large that similar small changes in the number of repeat units would have little effect of the properties of the polymer.

Generally, unless indicated differently elsewhere herein, suitable polymers of the invention may have a number average molecular weight ($M_n$) of ≧about 200 g/mol, preferably ≧about 400 g/mol, more preferably ≧about 800 g/mol, most preferably ≧about 1 kg/mol, usefully ≧about 2 kg/mol, more usefully ≧about 4 kg/mol, most usefully ≧about 8 kg/mol, conveniently ≧10 kg/mol, more conveniently ≧about 100 kg/mol and most conveniently ≧about 1000 kg/mol. Polymers having a relatively low mass, preferably ≦about 8 kg/mol, more preferably ≦about 4 kg/mol, and most preferably ≦about 1 kg/mol; may be referred to as oligomers.

The number average molecular weight as used herein (denoted by $M_n$) is determined by gel permeation chromatography (GPC) for example using an Alliance Waters 2690 GPC with two consecutive PL-gel columns, type Mixed-C, l/d=300/7.5 mm, (available from Polymer Laboratories, Amherst Mass. 01002, USA) with tetrahydrofuran (THF) as the eluent at 1 mL/min, at 50° C. and an Alliance Waters 2410 refractive index detector. A set of polystyrene standards (analysed according to DIN 55672) can be used to calibrate the GPC equipment.

Unless the context clearly indicates otherwise, as used herein plural forms of the terms herein are to be construed as including the singular form and vice versa. Thus, when referring to a specific moiety, e.g. "compound" or "polymer", this means "at least one" of that moiety, e.g. "at least one compound" respectively "at least one polymer", unless specified otherwise.

The term "comprising" as used herein will be understood to mean that the list following is non-exhaustive and may or may not include any other additional suitable items, for example one or more further feature(s), component(s), ingredient(s) and/or substituent(s) as appropriate.

The terms 'effective', 'acceptable' 'active' and/or 'suitable' (for example with reference to any process, use, method, application, preparation, product, material, formulation, compound, monomer, oligomer, polymer precursor, and/or polymers of the present invention and/or described herein as appropriate) will be understood to refer to those features of the invention which if used in the correct manner provide the required properties to that which they are added and/or incorporated to be of utility as described herein. Such utility may be direct for example where a material has the required properties for the aforementioned uses and/or indirect for example where a material has use as a synthetic intermediate and/or diagnostic tool in preparing other materials of direct utility. As used herein these terms also denote that a functional group is compatible with producing effective, acceptable, active and/or suitable end products.

One preferred utility of the macromolecules of present invention is as a reactive diluent, more preferably for radiation curable compositions, most preferably for compositions having a low viscosity before curing and low shrinkage during curing. Another utility of macromolecules of present invention is as a component which is suitable for use in compositions or formulations (e.g. inks, binders, coatings, adhesives, varnishes, paints and the like) with acrylate resins, such compositions being optionally radiation (e.g. UV) curable. As used herein 'acrylate resin' denotes any polymer obtained and/or obtainable from one or more acrylate and methacrylate monomers (and derivatives and/or analogues thereof) including copolymers with other monomers.

The terms 'optional substituent' and/or 'optionally substituted' as used herein (unless followed by a list of other substituents) signifies the one or more of following groups (or substitution by these groups): carboxy, sulpho, formyl, hydroxy, amino, imino, nitrilo, mercapto, cyano, nitro, methyl, methoxy and/or combinations thereof. These optional groups include all chemically possible combinations in the same moiety of a plurality (preferably two) of the aforementioned groups (e.g. amino and sulphonyl if directly attached to each other represent a sulphamoyl group). Preferred optional substituents comprise: carboxy, sulpho, hydroxy, amino, mercapto, cyano, methyl, halo, trihalomethyl and/or methoxy.

The synonymous terms 'organic substituent' and "organic group" as used herein (also abbreviated herein to "organo") denote any univalent or multivalent moiety (optionally attached to one or more other moieties) which comprises one or more carbon atoms and optionally one or more other heteroatoms. Organic groups may comprise organoheteryl groups (also known as organoelement groups) which comprise univalent groups containing carbon, which are thus organic, but which have their free valence at an atom other than carbon (for example organothio groups). Organic groups may alternatively or additionally comprise organyl groups which comprise any organic substituent group, regardless of functional type, having one free valence at a carbon atom. Organic groups may also comprise heterocyclyl groups which comprise univalent groups formed by removing a hydrogen atom from any ring atom of a heterocyclic compound: (a cyclic compound having as ring members atoms of at least two different elements, in this case one being carbon). Conveniently the non carbon atoms in an organic group may be selected from: hydrogen, halo, phosphorus, nitrogen, oxygen, silicon and/or sulphur, more conveniently from hydrogen, nitrogen, oxygen, phosphorus and/or sulphur.

The term 'silico' as used herein denotes species containing a silicon containing species analogous to organo for carbon Useful organic groups comprise one or more of the following carbon containing moieties: alkyl, alkoxy, alkanoyl, carboxy, carbonyl, formyl and/or combinations thereof; optionally in combination with one or more of the following heteroatom containing moieties: oxy, thio, sulphinyl, sulphonyl, amino, imino, nitrilo and/or combinations thereof. Organic groups include all chemically possible combinations in the same moiety of a plurality (preferably two) of the aforementioned carbon containing and/or heteroatom moieties (e.g. alkoxy and carbonyl if directly attached to each other represent an alkoxycarbonyl group).

Unless stated otherwise herein advantageous organo groups listed herein may comprise from 1 to 36 carbon atoms, more advantageously from 1 to 18, most advantageously from 1 to 12, especially from 1 to 10 inclusive, for example from 1 to 4 carbon atoms.

Unless specifically mentioned otherwise preferred organic moieties may comprise substituted and/or unsubstituted hydrocarbo moieties, hydrocarbo moieties which may (or may not) also comprise one or more heteroatoms (such as Si, S, N, O, P, or halogens), saturated hydrocarbon moieties, unsaturated hydrocarbon moities, organo-silicon compounds, any combinations thereof in the same moiety and/or mixtures thereof. Examples of suitable organic moieties include optionally substituted siloxane compounds/groups, alkanes, alkenes, alkynes, alkyls, alkylenes, alkenyls, (thio) esters, (thio)ethers, (thio)alcohols, carboxylic acids, amines, amides, nitrils. Examples of suitable substituents include halogens, phosphate groups, sulphates, nitrate groups.

More preferred organic moieties may comprise one or more oxygen atoms, most preferred organic moieties may comprise ethers and/or a hydroxylated hydrocarbon moieties.

The organic moiety may be linear or branched. The organic moiety may comprise one or more rings. Such ring may be aliphatic or aromatic.

An organic moiety, forming part of a macromolecule of the invention may for instance have 1 to 1000 carbon atoms, 1 to 100 carbon atoms or 1 to 50 carbon atoms. In particular for moieties other than the core (backbone) of the unsaturated compound (such as moiety X in the Formulae herein) such a moiety may comprise 1 to 30 carbon atoms, 1 to 20 carbon atoms, 1 to 10 carbon atoms or 1 to 6 carbon atoms.

The term 'hydrocarbo' group or moiety as used herein is a sub-set of a organic group and denotes any univalent or multivalent moiety (optionally attached to one or more other moieties) which consists of one or more hydrogen atoms and one or more carbon atoms and may comprise one or more saturated, unsaturated and/or aromatic moieties. Hydrocarbo groups may comprise one or more of the following groups. Hydrocarbyl groups comprise univalent groups formed by removing a hydrogen atom from a hydrocarbon (for example alkyl). Hydrocarbylene groups comprise divalent groups formed by removing two hydrogen atoms from a hydrocarbon, the free valencies of which are not engaged in a double bond (for example alkylene). Hydrocarbylidene groups comprise divalent groups (which may be represented by "$R_2C=$") formed by removing two hydrogen atoms from the same carbon atom of a hydrocarbon, the free valencies of which are engaged in a double bond (for example alkylidene). Hydrocarbylidyne groups comprise trivalent groups (which may be represented by "$RC\equiv$"), formed by removing three hydrogen atoms from the same carbon atom of a hydrocarbon the free valencies of which are engaged in a triple bond (for example alkylidyne). Hydrocarbo groups may also comprise saturated carbon to carbon single bonds (e.g. in alkyl groups); unsaturated double and/or triple carbon to carbon bonds (e.g. in respectively alkenyl and alkynyl groups); aromatic groups (e.g. in aryl groups) and/or combinations thereof within the same moiety and where indicated may be substituted with other functional groups The term 'alkyl' or its equivalent (e.g. 'alk') as used herein may be readily replaced, where appropriate and unless the context clearly indicates otherwise, by terms encompassing any other hydrocarbo group such as those described herein (e.g. comprising double bonds, triple bonds, aromatic moieties (such as respectively alkenyl, alkynyl and/or aryl) and/or combinations thereof (e.g. aralkyl) as well as any multivalent hydrocarbo species linking two or more moieties (such as bivalent hydrocarbylene radicals e.g. alkylene).

Any radical group or moiety mentioned herein (e.g. as a substituent) may be a multivalent or a monovalent radical unless otherwise stated or the context clearly indicates otherwise (e.g. a bivalent hydrocarbylene moiety linking two other moieties). However where indicated herein such monovalent or multivalent groups may still also comprise optional substituents. A group which comprises a chain of three or more atoms signifies a group in which the chain wholly or in part may be linear, branched and/or form a ring (including spiro and/or fused rings). The total number of certain atoms is specified for certain substituents for example $C_{1-N}$organo, signifies a organo moiety comprising from 1 to N carbon atoms. In any of the formulae herein if one or more substituents are not indicated as attached to any particular atom in a moiety (e.g. on a particular position along a chain and/or ring) the substituent may replace any H and/or may be located at any available position on the moiety which is chemically suitable and/or effective. It will be appreciated that moieties that inherently comprise a ring (for example cycloalkyl or aromatic moieties such as aryl) must contain at least 3 atoms (preferably carbon atoms) to form the ring. Similarly it will understood that other moieties will have a minimum number of atoms (which may or may not be stated) for example aralkyl or alkylaryl moieties must comprise at least 4 atoms (at least 3 for the aryl and at least one for the alkyl).

As used herein chemical terms (other than IUAPC names for specifically identified compounds) which comprise features which are given in parentheses—such as (alkyl)crylate, (meth)acrylate and/or (co)polymer—denote that that part in parentheses is optional as the context dictates, so for example the term (meth)acrylate denotes both methacrylate and acrylate.

The substituents on the repeating unit of a polymer and/or oligomer may be selected to improve the compatibility of the materials with the polymers and/or resins in which they may be formulated and/or incorporated for the uses described herein. Thus the size and length of the substituents may be selected to optimise the physical entanglement or interlocation with the resin or they may or may not comprise other reactive entities capable of chemically reacting and/or cross-linking with such other resins as appropriate.

Certain moieties, species, groups, repeat units, compounds, oligomers, polymers, materials, mixtures, compositions and/or formulations which comprise and/or are used in some or all of the invention as described herein may exist as one or more different forms such as any of those in the following non exhaustive list: stereoisomers (such as enantiomers (e.g. E and/or Z forms), diastereoisomers and/or geometric isomers); tautomers (e.g. keto and/or enol forms), conformers, salts, zwitterions, complexes (such as chelates, clathrates, crown compounds, cyptands/cryptades, inclusion compounds, intercalation compounds, interstitial compounds, ligand complexes, organometallic complexes, non-stoichiometric complexes, π-adducts, solvates and/or hydrates); isotopically substituted forms, polymeric configurations [such as homo or copolymers, random, graft and/or block polymers, linear and/or branched polymers (e.g. star and/or side branched), cross-linked and/or networked polymers, polymers obtainable from di and/or tri-valent repeat units, dendrimers, polymers of different tacticity (e.g. isotactic, syndiotactic or atactic polymers)]; polymorphs (such as interstitial forms, crystalline forms and/or amorphous forms), different phases, solid solutions; and/or combinations thereof and/or mixtures thereof where possible. The present invention comprises and/or uses all such forms which are effective as defined herein.

Other conventional terms from polymer science that are used herein (such as polymer, monomer, oligomer etc) shall have those meanings recommended by IUPAC and as defined in Pure Appl. Chem., Vol. 68, No. 12, pp. 2287-2311, 1996, the contents of which are incorporated herein by reference.

In a preferred embodiment, the macromolecule of the invention (which is not a dendrimer) is represented by Formula I.

Formula I where

X is an organo, silcio or organo-silico moiety, n is 0 or an integer of at least 1, m is an integer of at least 1; and the sum of n and m (also referred to herein as "k") is $\geq 1$, Y is represented by Formula II.

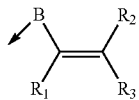

Formula II where
R$_1$, R$_2$ and R$_3$ are each independently selected from the group of hydrogen and hydrocarbo moieties; and
B represents a moiety selected from the group consisting of: carbonyloxy [—(C=O)O—], oxycarbonyl [—O(C=O)—] and oxy [—O—]; and
Z is represented by Formula III

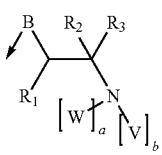

Formula III where
B, R$_1$, R$_2$ and R$_3$ are each independently as defined herein, for Formula II.
a is 0 or 1, b is 1, 2 or 3, and the sum of a and b (also referred to herein as "c") is 2 or 3,
W is hydrogen, alkyl or V; and
V is each independently represented by one of Formulae IV to VI:

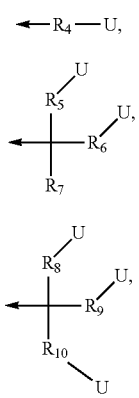

Formula IV
Formula V
Formula VI where
R$_4$, R$_5$, R$_6$, R$_8$, R$_9$ and R$_{10}$ are each independently organo groups;
U is each independently selected from the group consisting of: hydroxy, carbonyl-R$_{11}$ [—(C=O)R$_{11}$] and moieties represented by Formulae VII and VIII:

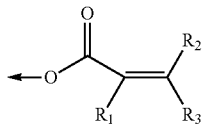

Formula VII

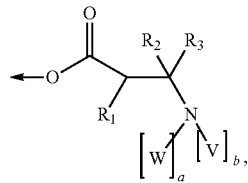

Formula VIII where:
V, W, R$_1$, R$_2$, R$_3$, a and b are each independently as defined herein for Formulae II and III; and
R$_{11}$ is an organo group.

Some of the Formulae herein represent radical moieties where the arrow represents the point of attachment of these radicals to another moiety (for example the rest of the macromolecule of Formula I). The Formulae herein represent all isomers thereof. For example Formula III may contain several chiral centres and if Formula I and II are different Formula I may contain a chiral centre at X. All enantiomers and mixtures thereof (e.g. racemates) are encompassed by these Formulae.

In Formula I, k (=n+m) is preferably $\geq 2$, more preferably $\geq 3$. Usually k is $\leq 20$, in particular $\leq 16$, more particularly $\leq 10$. For practical reasons, k may be $\leq 6$, usefully $\leq 5$, more usefully $\leq 4$.

In Formula II, R$_1$ is conveniently selected from the group of consisting of: hydrogen and alkyl, preferred alkyl being C$_{1-20}$ alkyl, more preferably C$_{1-6}$alkyl, most preferably methyl.

In Formula II, R$_2$ and R$_3$ are preferably each independently selected from the group consisting of: hydrogen, alkyl and carboxylate groups, where the carboxylate groups are optionally protonated or provided with another cation, more preferred alkyl and/or carboxylates comprise 1-20 carbon atoms, most preferably 1-6 carbon atoms. Conveniently R$_2$ and/or R$_3$ are each independently hydrogen or methyl.

In Formula II, B is preferably oxy carbonyl [—O(C=O)—] and Formula II represents an alpha beta unsaturated ester moiety.

In Formula III, c (=a+b) is preferably 2. If c is 3 the nitrogen atom in Formula III is positively charged and Formula I may represent a salt with a counter anion (and/or may be zwitterionic).

In Formula III, where W is an alkyl, it is preferably C$_{1-30}$alkyl, more preferably C$_{1-20}$alkyl, most preferably C$_{1-10}$alkyl.

In Formulae IV to VI and moiety U, R$_4$, R$_5$, R$_6$, R$_8$, R$_9$, R$_{10}$ and R$_{11}$ are preferably each independently selected from the group consisting of:
organo groups comprising one or more heteroatoms optionally selected from C, N, O and Si; and/or
substituted organo groups optionally substituted with one or more hydroxyl, carboxy and/or amino groups.

More preferred R$_4$, R$_5$, R$_6$, R$_8$, R$_9$, R$_{10}$ and R$_{11}$ are each independently selected from optionally substituted alkyl (including cycloalkyl) and aromatic groups.

Conveniently R$_4$, R$_5$, R$_6$, R$_8$, R$_9$, R$_{10}$ and R$_{11}$ independently may be optionally substituted C$_{1-30}$hydrocarbo, more conveniently optionally substituted C$_{1-20}$hydrocarbo, most conveniently optionally substituted C$_{1-10}$hydrocarbo.

In Formulae V or VI any of R$_5$, R$_6$, R$_8$, R$_9$, independently may be absent in which case the —O—U moiety is directly attached to the carbon attached to the nitrogen shown in Formula III.

In Formulae V or VI $R_7$ and $R_{10}$ are each independently selected from the group of hydrogen and hydrocarbo moieties, including hydrocarbo moieties comprising one or more heteroatoms and hydrocarbo moieties comprising substituents. $R_7$ and $R_{10}$ may comprise $\leqq 30$ carbon atoms, usefully $\leqq 20$ more usefully $\leqq 10$. Preferably $R_7$ and $R_{10}$ are each independently optionally substituted $C_{1-6}$alkyl or hydrogen.

For macromolecular compounds comprising more than one $R_1$, $R_2$, $R_3$, $R_4$, $R_5$, $R_6$, $R_8$, $R_7$, $R_9$, $R_{10}$, $R_{11}$, Z, Y, U, W, V, B, a, b, c, k, n, m, each may be selected independent of radicals/moieties/constants of the same and different type. For example, for a macromolecular compound where n is 2, the B-segments of the Y-segments need not be the same; for example one B-segment may comprise an ester moiety (—O (C=O)—) and the other B-segment may comprise an ether moiety (—O—). Where formulae include chiral atoms and/or geometric isomers, all suitable stereoisomers are encompassed by the formulae herein.

In a highly preferred embodiment, the macromolecular compound comprises at least 1 olefinically unsaturated polymerisable group (which is a UV reactive group) to allow for further polymerisation via UV-curing. More preferably the macromolecular compound comprises at least 2 and in particular 4 to 16 olefinically unsaturated polymerisable groups. The olefinically unsaturated polymerisable group(s) may be arranged in X or in any of the branches or end groups of the branches of the macromolecular compound. Preferably at least some of the olefinically unsaturated polymerisable group(s) is/are arranged in the end groups of the branches.

X can be a based on a silanol, in particular it may be an inorganic silicate or an organo-silicate.

Preferably X is an organic moiety, which optionally comprises one or more heteroatoms and which optionally comprises one or more substituents; heteroatoms (e.g. halogen or nitrogen) may be present in the chain or as a substituent, e.g. to modify solubility properties in a solvent of choice wherein the method according to the invention may be carried out.

In an embodiment, X comprises one or more aromatic rings. For instance X may at least conceptually be the residue of bisphenol or of alkoxylated bisphenol. In an embodiment, X comprises a pyrine, a diazine or a triazine. The presence of one or more cyclic structures (especially one or more aromatic rings) may improve thermal and/or mechanical stability of the macromolecular compound or a polymer composed thereof.

X may in particular comprise up to 1000 carbons, more in particular up to 100 or up to 50 carbons. X usually comprises at least 1 carbon, at least 2, at least 3, at least 5, at least 10 or at least 20 carbon atoms. A relatively high chain length (of carbons and optionally one or more heteroatoms, at least predominantly linked by saturated bonds) may be advantageous for reduced shrink upon curing. A compound wherein the X moiety is relatively small may be advantageous for improved water resistance, in case X is a hydrophilic moiety, e.g. a moiety at least predominantly composed of ethylene oxide moieties.

In an embodiment, X is selected from the group of alkyl (k=1) and alkylene (k>1) moieties.

In an embodiment X may be a hydrocarbo group, such as an alkyl or alkylene residue of an esterified alcohol comprising one or more hydroxyl groups, wherein the number of hydroxyl groups determines the upper limit for k.

X may be the residue of a diol, in particular of ethylene glycol, propyleneglycol, neopentyl glycol or hexane diol (to form a compound of formula 1 wherein k is up to 2).

X may be the residue of a triol, in particular of glycerol, of trimethylol propane (TMP) or of an alkoxylated triol (to form a compound of formula 1 wherein k is up to 3), in particular ethoxylated TMP (EOTMP), ethoxylated glycerol, propoxylated glycerol.

X may be the residue of a tetraol, in particular of ditrimethylol propane pentaerythritol or of an alkoxylated tetraol, in particular ethoxylated pentaerythritol (to form a compound of formula 1 wherein k is up to 4).

X may be the residue of a pentol, e.g. a polyglycerol (for instance based on three glycerol units).

X may be the residue of a hexyl, in particular dipentaerythritol.

X may be an OH functional highly branched polymeric moiety.

X may be the residue of an organic acid, a salt thereof or an anhydrides thereof, in particular such acid, salt or anhydride having two or more functionalities, more particularly an acid, salt and/or anhydride thereof (optionally having 1 to 20 carbon atoms) such as those selected from the group of: adipic acid, succinic acid, maleic acid fumaric acid, phthalic acid, salts thereof and anhydrides thereof.

X may represent a polymeric moiety, preferably selected from the group of polyether moieties, polyester moieties, polyurethane moieties and polyepoxy moieties.

In an advantageous embodiment, X comprises an alkylene oxide or a polyalkylene oxide group, optionally each alkylene unit independently comprising 1 to 6, preferably 1 to 4 carbon atoms. More preferred polyalkylene moieties may be (poly) ethylene oxide, (poly)propylene oxide and/or (poly)butylene oxide. The polyalkylene oxide may be a copolymer of two or more different alkylene oxides, such as a copolymer of at least two moieties selected from the group of ethylene oxide, propylene oxide and butylene oxide. The number of alkylene oxide or glycerol units or the type of alkylene may affect the degree to which macromolecules of the invention are soluble in a particular solvent or can be diluted with a particular diluent. For instance, the presence of poly(ethylene)oxide may improve water solubility of the macromolecule and its dilutability with water, and relatively long poly(ethylene) oxides may improve this to a greater extent compared to relatively short chains.

Other preferred moieties that may comprise X can be determined from the preferred unsaturated compounds described herein (which form the core molecule) from which macromolecules according to the invention can be made.

Macromolecules of the invention may be prepared in two stages. The first step is Michael addition reaction (reaction a), where (without wishing to be bound by any mechanism) it is generally believed that a nitrogen of an amine forms a bond with the β-carbon of an ethylenically unsaturated group and a hydrogen forms a bond with the α-carbon of the same ethylenically unsaturated group. Suitable conditions are described in the prior such as some of those documents mentioned herein. The reaction is usually carried out in a liquid phase. The liquid may be an aliphatic or aromatic hydrocarbon, such as methylcyclohexane or toluene. The temperature may in particular be from ambient temperature (e.g. 20° C.) up to the boiling point (under reaction conditions) of the amine.

The esterification b) can be carried out under essentially the same conditions as the addition reaction a). If desired, the esterification can be carried out in the same reaction system as addition reaction a), i.e. reaction b) can be carried out in the presence of reagents for reaction a) and vice versa.

The olefinic unsaturation introduced by the esterification reaction may be subjected to a (further) Michael-type addition or provides a polymerisable moiety. Thus the macromolecular compound may be subjected to a polymerisation reaction to form a polymer comprising a plurality of polymerised macromolecular compound units. Accordingly, the invention further relates to a polymer composed of polymerisable macromolecular compounds according to the invention and optionally one or more other polymerisable compounds.

Advantageously, the method may be carried out in a "one-pot" process, i.e. where one or more reactions a) are allowed to take place in the presence of reagent for reaction b) and wherein, one or more reactions b) may take place in the presence of reagent for reaction a). A one pot process can also be used if further reactions a) and optionally further reactions b) are carried out. Thus, it is not necessary to carry out subsequent reactions in isolation of each other, although this is—in principle—possible.

Advantageously a compound according to the invention may be (photo-) cured, also in the absence of a separate catalyst. It has been found possible to provide a liquid macromolecular compound (at 25° C.), in particular a liquid macromolecule having a relatively low viscosity (at a particular molecular weight), compared to similar known macromolecule having the same molecular weight.

In general a macromolecule of the invention has a viscosity of $\leq 25$ Pa·s, preferably $\leq 10$ Pa·s. The term "viscosity" used herein means the Brookfield viscosity at 25° C., measured by the method described in ISO 2555-89. In particular it has been found possible to prepare macromolecules of the invention with a viscosity of $\leq 2$ Pa·s, in particular $\leq 1.5$ Pa·s, more in particular $\leq 1.0$ Pa·s, especially $\leq 750$ mPa·s. Thus, macromolecules of the invention may be used in applications requiring medium (2 to 10 Pa·s) or low (<2 mPa·s) viscosities, and only a small amount (or even no) diluent need be added, and the properties of the product will not be detrimentally affected (or at least not to an unacceptable extent) by the presence of diluent.

The viscosity of the macromolecule of the invention may be $\geq 50$ mPa·s, usually $\geq 100$ mPa·s, more usually $\geq 200$ mPa·s, most usually $\geq 300$ mPa·s. Relatively large macromolecules of the invention may conveniently have a viscosity $\geq 500$ mPa·s, for example $\geq 700$ Pa·s.

Macromolecules of the invention may usefully be diluted with a suitable amount of water and mixed to form a homogenous mixture. More useful macromolecules may be added in a suitable amount to water and mixed to dissolve therein to form a homogenous solution.

The macromolecules may be mixed with a relatively high amount of water or other hydrophilic liquid, preferably $\leq 50\%$, more preferably $\leq 70\%$, of hydrophilic liquid by weight. Viscosity can be considerably reduced by diluting the macromolecule with a relatively low amount of water or another hydrophilic liquid, preferably from 1 to 20%, more preferably from 5 to 10%, of hydrophilic liquid by weight. The weight percentages are weight of hydrophilic liquid by total weight of hydrophilic liquid plus macromolecule.

Macromolecules of the invention can thus replace substantially, or even entirely, those reactive diluents of low molecular weight that are conventionally added to formulations to lower their viscosity (to <0.5 Pa·s or even <0.3 Pa·s), to be suitable for uses such as spraying, ink-jet printing, flexography, offset printing, gravure printing and/or other graphic art processes.

The applicant has found that macromolecules of the invention may be applied to a substrate and cured (polymerised and/or dried) to form a coating which adheres well to the substrate. Thus the macromolecules may be advantageously used (in whole or as a part thereof with other components) as for example: an adhesive, a coating, an ink, a cross linker, a rheology modifier, a dispersing agent (e.g. for a pigment) and/or an adhesion promoter.

These macromolecules may also be used in any application wherein acrylate resins are used. Such applications include: (as a resin) in food packaging, in graphic arts (e.g. as protective coating, as an ink-receptive layer, as in ink, for example for ink-jet) in automotive applications, wood coatings, paper coatings, varnishes, over print varnishes (OPV), film coatings, plastic coatings, adhesives, coil coatings, metal coatings, concrete, flexible flooring, parquet, joinery, flexo printing, offset printing and gravure printing.

Another embodiment of the invention provides a radiation curable (preferably UV curable) composition comprising:
a) from 1 to 99% by weight of radiation curable monomers;
b) from 1 to 99% by weight of one or more non-dendrimeric macromolecules of the invention as described herein (and/or dendrimers prepared in an analogous manner) optionally as reactive diluent;
c) optionally from 0 to 10% of one or more photo-initiator(s) where the weight percentages are calculated from the total of a), b) and c) which total 100%; and
where preferably the composition exhibits one (preferably two, more preferably three) of the following properties
i) low shrink on curing (preferably less than 10% shrink, more preferably <5%, most preferably <2%);
ii) high speed cure, (preferably being substantially cured after irradiation at an energy of 600 mJcm$^{-2}$, more preferably 400 mJcm$^{-2}$, most preferably 200 mJcm$^{-2}$); and/or
iii) low viscosity (preferably less than 10 mPa·s, preferably <2 mPas, more preferably <0.5 mPas).

Shrink can be measured as a change (decrease) in the area of an uncured coating applied to a conventional plastic test substrate (as described herein) compared to the area of the coating immediately after curing.

One other embodiment of the invention provides for use of one or more non-dendrimeric macromolecules of the invention as described herein (and/or dendrimers prepared in an analogous manner) in the manufacture of a radiation curable composition of the invention for the purpose of imparting low shrink, high cure speed and/or low viscosity thereto.

A still other embodiment of the invention provides for use one or more non-dendrimeric macromolecules of the invention as described herein (and/or dendrimers prepared in an analogous manner) as reactive diluents for a polymerisible composition.

Process

It is preferred that the amount of the hydroxyl functional amine added in step 'a' should be in stoichiometrical ratio with or in stoichiometrical excess with the number of olefinically unsaturated groups in the olefinically unsaturated compound. This results in an hydroxyl functional addition product which is substantially saturated as substantially all the unsaturated groups have undergo a Michael addition.

In a special embodiment, the molar ratio of amine to olefinically unsaturated carboxylic acid is at least 1.01, in particular at least 1.05 more in particular at least 1.10, even more in particular at least 1.15 or at least 1.25. The ratio is usually up to 2, in specific embodiment it may be up to 1.75 or up to 1.5.

The addition product from step 'a' is used to prepare a branched macromolecule in step 'b' by esterifying the hydroxy groups of the addition product with an olefinically unsaturated carboxylic acid (or derivative thereof). The resultant olefinically unsaturated ester formed in step 'b', can undergo a (further) Michael-type addition reaction with an amine comprising at least two hydroxyl groups in further step 'a'. The resultant addition product can be esterified as before in a further step 'b'. Thus it is possible to increase the number of functional groups (unsaturated groups/hydroxyl groups)

with each cycle of reactions 'a' and 'b' to prepare a hyperbranched macromolecule. However macromolecules of the invention are not dendrimers In a preferred embodiment, the olefinically unsaturated compound (used as a core molecule for providing the addition product of reaction a) is represented by formula IX

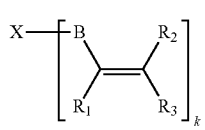

Formula IX

Where k (=n+m), X, B, $R_1$, $R_2$ and $R_3$ are each independently as defined herein.

In Formula IX it is preferred that k is at least 1, more preferably at least 2, most preferably at least 3. Usually k is 20 or less, in particular 16 or less, more in particular 10 or less. For practical reasons, k preferably is 6 or less, 5 or less, or 4 or less.

In a particularly preferred embodiment, suitable olefinically unsaturated compounds that may form the core of macromolecules of the invention may be selected from the group consisting of: (poly)ethylene glycol di(meth)acrylates and (poly)propylene glycol di(meth)acrylates. Such compounds advantageously produce liquid macromolecules of low viscosity for a given molecular mass and/or which exhibit good adhesion properties. Such macromolecules may be diluted with water, if desired, to further reduce viscosity.

Convenient multi-functional (e.g. di, tri or tetra functional) olefinically unsaturated compounds which may be used as a core molecule may comprise:
dipropylene glycol diacrylate (DPGDA),
tripropylene glycol diacrylate (TPGDA),
diethyleneglycol diacrylate,
di(meth)acrylates of aliphatic diols, such as 1,6-hexanediol di(meth)acrylate, neopentylglycol diacrylate (NPGDA), and/or butanediol diacrylate (BDDA).
bisphenol A di(meth)acrylate,
ethoxylated and/or propoxylated bisphenol A di(meth)acrylate,
neopentylglycol di(meth)acrylate,
ethoxylated and/or propoxylated neopentylglycol di(meth)acrylate.
trimethylpropane tri(meth)acrylate;
alkoxylated (e.g. ethoxylated and/or propoxylated) trimethylpropane tri(meth)acrylate; glycerol tri(meth)acrylate;
alkoxylated (e.g. ethoxylated and/or propoxylated) glycerol tri(meth)acrylate;
tris(hydroxyalkyl)isocyapurate tri(meth)acrylates, such as those where the hydroxyalkyl is 2-hydroxyethyl;
pentaerythritol tri(meth)acrylate;
alkoxylated (e.g. ethoxylated and/or propoxylated) pentaerythritol tri(meth)acrylate; pentaerythritol tetra(meth) acrylate;
alkoxylated (e.g. ethoxylated and/or propoxylated) pentaerythritol tetra(meth)acrylate.

Compounds with four (meth)acrylate groups may provide an ester (as core molecule) that has four unsaturated bonds that can take part in the Michael-type addition.

In a particularly preferred embodiment the olefinically unsaturated compound is selected from the group consisting of:
trimethylolpropane tri(meth)acrylate (TMPT(M)A),
hexanediol di(meth)acrylate (HDD(M)A),
dipropyleneglycol di(meth)acrylate (DPGD(M)A),
tripropyleneglycol di(meth)acrylate (TPGD(M)A),
neopentylglycol di(meth)acrylate (NPGD(M)A),
pentaerythritol tetra(meth)acrylate (PET(M)A),
pentaerythritol tri(meth)acrylate ($PET_3$(M)A),
idodecyl(meth)acrylate (ID(M)A),
glycedyl(meth)acrylate,
ethoxyethoxyethyl(meth)acrylate (EOEOE(M)A),
glycerolpropoxy tri(meth)acrylate (GPT(M)A),
isobornyl(meth)acrylate (iBo(M)A),
isooctyl(meth)acrylate,
tridecyl(meth)acrylate,
caprolacton(meth)acrylate,
nonylphenol(meth)acrylate,
allyl(meth)acrylate,
phenoxyethyl(meth)acrylate (PE(M)A),
cyclohexanedimethanoldi(meth)acrylate,
Diethyleneglycol di(meth)acrylate,
butanedioldi(meth)acrylate,
bisphenol-A di(meth)acrylate,
dipentaerythritol hexa(meth)acrylate,
polyethyleneglycol di(meth)acrylate (PEGD(M)A),
methoxypolyethylene glycol mono(meth)acrylate,
polypropyleneglycol di(meth)acrylate,
tetrahydrofurfuryl(meth)acrylate,
tris(2-hydroxyethyl)isocyanurate tri(meth)acrylate,
stearyl(meth)acrylate,
lauryl(meth)acrylate,
phenol(meth)acrylate,
ditrimethylol propane tetra(meth)acrylate (diTMPT(M)A),
ditrimethylol propane penta(meth)acrylate (diTMPP(M)A),
hydroxylethyl (meth)acrylate (HE(M)A); and/or suitable mixtures thereof.

Further, ethoxylated or propoxylated derivatives of these molecules are particularly preferred. In as far as said particularly preferred compounds comprise more than one (meth)acrylate, all (meth)acrylates may be acrylates, all may be methacrylates, or the compounds may comprise both an acrylate and a methacrylate.

As an amine, preferably a secondary amine comprising two hydroxylated hydrocarbon groups is used. Such amine is represented by the formula $R^x$—NH—$R^y$, wherein $R^x$ and $R^y$ are independently selected from the group of hydroxylated hydrocarbons. In particular $R^x$ and/or $R^y$ may be independently selected from hydroxy-alkyl moieties and polyether-ol moieties. The polyether-ol moiety may in particular be selected from polyethylene oxide moieties and polypropylene oxide moieties. The hydroxyalkyl may in particular be a $C_{1-6}$ hydroxyalkyl. Preferably diethanol amine or dipropanol amine are used. Of these good reactivity in the esterification has been found without needing a catalyst.

For reaction b), in principle any olefinically unsaturated carboxylic acid can be used, including any salt, anhydride, ester or acid halogenide thereof. In case an olefinic unsaturation of such compound should be capable of participating in a (further) reaction a) after esterification, the unsaturated carboxylic acid is preferably an α,β-olefinically unsaturated acid, in particular such an unsaturated ester selected from the group of acrylic acid, methacrylic acid, crotonic acid, fumaric acid and maleic acid (including any salt, anhydride, ester or acid halogenide thereof).

As indicated above, a product of a reaction b) can react in a further reaction a), of which the resultant addition product may take part in a further esterification reaction. Thus, the level of increase in olefinic unsaturations after each subsequent reaction b) can in principle be adjusted for instance by using a (secondary) amine comprising more than two hydroxyl groups. For instance, with an amine comprising three hydroxyl groups, the number of unsaturations may triple with each generation.

It is also possible to react at least part of the hydroxyl groups with an anhydride, in particular a cyclic anhydride, to form an acid functional compound, which can subsequently be reacted with a hydroxy functional compound, for example a hydroxy alkyl(meth)acrylate (e.g. hydroxylethyl(meth)acrylate), an alkoxylated alkyl ester (e.g. a ethoxylated methyl ester), or a polyol such as mentioned herein for X.

It is also possible to react at least a number of the hydroxyl groups of an addition product obtained by a reaction a) with a saturated compound. In particular the hydroxyl groups may be esterified or etherified with a saturated compound. Such reaction may be used to modify one or more product properties, in particular to modify wettability, viscosity, adhesion to a substrate or shrinking tendency (upon curing). Preferably, such esterification or etherification comprises reacting a hydroxyl group with a carboxylic acid, in particular a fatty acid (as a free acid, an anion of the acid or a fatty acid anhydride), a polyalkoxylate, a polyalkoxy anhydride.

Preferred fatty acids include $C_{12-22}$ saturated acids and $C_{12-22}$ unsaturated acids. In particular the fatty acid may be lauric acid, soy acid, linoleic acid, sunflower acid, oleic acid, stearic acid, coconut acid, recinoleic acid and/or palm acid.

Preferred polyalkoxylate respectively anhydrides thereof include polyethylene oxide and polypropylene oxide respectively anhydrides thereof.

Polyethylene oxide may for instance be used to increase hydrophilicity of the macromolecular compound, and thus improve miscibility with a hydrophilic diluent or solvent, such as water.

In a special embodiment it is envisaged that a polyalkylene oxide may also improve anti-fouling properties of a coating made from a macromolecular compound of the invention, e.g. it may contribute to reduced microbial adherence to the coating.

It is also possible to react a part of the OH groups originating from the amine with an inorganic acid, for instance phosphoric acid, sulphuric acid, nitric acid or another strong acid. Thus a product property may be altered. For example fire retardancy may be improved (by including phosphate groups) or the adhesion properties to a specific substrate may be improved, e.g. adherence to a metallic material.

It is also possible to leave a part of the OH groups originating from the amine free. Thus a macromolecular compound is provided with one or more reactive hydroxyl groups. Such compound may for instance be used in the preparation of a polymer such as a polyurethane or a polyester.

It should be noted that the degree of further branching in a subsequent reaction a) will be less, the more hydroxyls are reacted with saturated compounds. Thus, for providing a hyperbranched macromolecular compound it is preferred to carry out such reaction only after the last reaction b) or to carry out such reaction before a last reaction b) on only a minor fraction (e.g. less than 25%) of the hydroxyls.

Further, usually no (or very few) unsaturations will be present for further polymerisation of the macromolecular compound, if substantially all hydroxyls are reacted with a saturated compound (such as a saturated carboxylic acid, a saturated polyalkoxylate or anhydride thereof). Such macromolecular compound may be useful, e.g., as a dispersant for a pigment or other particulate material or as a rheology modifier, e.g., in a coating composition such as a paint, or in an ink. However, if the macromolecular compound is intended to be suitable for further polymerisation via UV-curing, the macromolecular compound must comprise UV reactive groups (such as reactive unsaturations) and it is preferred that for example 50-100% of the hydroxyls are esterified with an unsaturated carboxylic acid.

Thus, the number of olefinically unsaturated polymerisable groups may range from 2 to 32, or higher. In particular it may be up to 2, 3, 4, 6, 8, 9, 12 or 16.

The invention further relates to a composition comprising a macromolecular compound or polymerised macromolecular compound according to the invention, in particular a liquid composition, such as a liquid solution or a liquid dispersion. In particular, the composition may be selected from the group of coating compositions, inks, toners and adhesives.

A composition of the invention may in particular further comprise one or more additives selected from the group consisting of: diluents (for instance water, organic diluents); colorants for example pigments, such as inorganic pigments (e.g. $TiO_2$, ZnO), organic pigments (e.g. nickel azo, arylamide, phenal, lithol, naphtol-AS, phthalocyane, carbon black, etc), effect pigments (e.g. fluorescence pigments, metal pigments (aluminium, bronze), nacreous pigments); and/or dyes; flow agents, for instance methyl diethanol amine (MDEA); levelling agents; anticrater-agents; initiators, in particular benzophenone or another photo-initiator; adhesion modifiers; viscosity modifiers; tackifiers; wax, dispersants; synergists, wetting agents (in particular pigment wetting agents); silicones, slip additives (e.g. polydimethyl siloxane, polyether siloxane); anti-block agents; surface tension reducing agents; fillers (e.g. calcium carbonates, talc); matting agents (e.g. sulfosuccinates); adhesion promoters; rheology modifiers; UV-stabilisers; defoamers; thickeners; further polymers, for instance selected from the group of poly(meth)acrylates, poly(vinyl)esters and polyolefins; any suitable combinations thereof; and/or any suitable mixtures thereof.

The invention further relates to a substrate provided with macromolecule(s) of the invention, for example a cured coating thereon prepared or preparable from a macromolecule according to the invention. The substrate may be selected from the group consisting of: polymeric materials, metals, ceramics, glass, textile, wood and paper. The (cured) macromolecular compound may form a coating (such as a protective coating), a decorative pattern, or present information (e.g. a print containing text, a figure or the like).

Many other variations embodiments of the invention will be apparent to those skilled in the art and such variations are contemplated within the broad scope of the present invention. Further aspects of the invention and preferred features thereof are given in the claims herein.

EXAMPLES

The present invention will now be described in detail with reference to the following non limiting examples which are by way of illustration only. The following examples are prepared using the Standard Method below with reference to Table 1 herein (1a, 1b, 1c and 1d). Where the Standard Method is modified to prepare an Example, this is indicated below.

Standard Method

A macromolecule is prepared by reacting a first functional species ('ACR1') ('a' mol) ($M_n$~'b' daltons) with a multi hydroxyl functional amine (AM(OH)) ('c' mol) for 'd' hour at 'e' ° C. Solvent (SOL) ('f' g), methoxy phenol (MP) ('g' ppm), phenotiazine (PT) ('h' ppm), nitrobenzene (NB) ('i' ppm) and tris(nonylphenyl) phosphite (TNPP) ('j' ppm) are added to the reaction mixture, for radical and colour stabilisation. Then a second functional species ('ACR2') ('k' mol) and radical stabilizers (MP('l' ppm) and PT('m' ppm)) to prevent radical polymerisation are introduced into the reactor with gas (GAS). If the gas is air ($O_2$) it is bubbled through the reaction mixture to inhibit polymerisation. If the gas is nitrogen ($N_2$) it is passed over the reaction mixture at a flow rate of about 'n' g/min. The mixture is then heated and kept within a temperature range of 'o' ° C. under reflux conditions. The water produced by condensation is removed via a Dean Stark apparatus. After 'p' hours excess ACR2 and solvent are removed by distilling under reduced pressure (at 'q' mbar).

The presumed formula of the product of each example is given after the table, where (if present) the average number of certain repeat units in each formula (n', or the sum of x' y' and z') is given in the Table.

Each example is characterized by the data in the Tables where:

'r' describes the morphology of the product at 25° C. (liq=liquid),

's' denotes its Brookfield viscosity (BV) in mPa·s (measured at T rpm),

'u' denotes the actual average number of acrylic functional groups (Nbr Ac) per product molecule as determined by proton NMR;

'v' denotes the percentage conversion (% conv.) of the hydroxyl groups present in the product from step (a) that were esterified in step (b). Where % conv. <100% this indicates an incomplete conversion where the final product also comprises molecules in which one or more hydroxy groups have not been esterified; and 'w' denotes the theoretical average number of acrylic functional groups per product (Max Ac) if 100% of the hydroxy groups are esterified.

The abbreviations used above and in Table 1 are as follows:
AA=acrylic acid,
AM(OH)=multi OH functional amine,
ACR1=first functional species (e.g. compound or oligomer), usually an acrylate or methacrylate,
ACR2=second functional species (e.g. compound or oligomer), usually an acrylate or methacrylate and may be the same or different from ACR1,
DEA=diethanol amine,
DEGDA=diethylene glycol diacrylate,
diTMPPMA=ditrimethylol propane penta-methacrylate,
DPA=diisopropanol amine,
DPGDA=dipropylene glycol diacrylate,
HEA=hydroxylethyl acrylate;
HDDA=the compound, 1,6 hexanediol diacrylate,
IPA=isopropyl acetate, a solvent,
MCH=methyl cyclohexane, a solvent,
MDEA=n-methyl diethanol amine,
MP=methoxy phenol, an inhibitor of radical polymerisation,
NB=nitrobenzene,
NPA=n-propyl acetate, a solvent,
PEGDA=an oligomer polyethyleneglycol diacrylate (having a $M_n$ given in the Table),
PEN=2-pentanone, a solvent,
PETA=pentaerythritol tetra-acrylate,
PT=phenotiazine, an inhibitor of radical polymerisation,
SOL=solvent,
TBHQ=tert-butyl hydroquinone, an inhibitor of radical polymerisation,
TOL=toluene, a solvent,
TMP(EO)PA=an oligomer ethoxylated trimethylol propane penta-acrylate (having a $M_n$ given in the Table),
TMP(EO)TA=an oligomer ethoxylated trimethylol propane triacrylate (having a $M_n$ given in the Table),
TMPTA=trimethylol propane triacrylate, and
TNPP=tris(nonylphenyl) phosphate, an inhibitor of radical polymerisation The Examples 1 to 15 are illustrated by respective Formulae 1, 2, 3, 5, 6, 7, 10, 12, 13, 14a, 14b and 15 below (i.e. for convenience Formulae 4, 8, 9, 11 have been omitted).

TABLE 1a (data to 3sf)

| Ex | ACR1 | a ACR1 (mol) | b ACR1 ($M_n$) | AM (OH) | c (mol) | d (hr) | e (° C.) |
|---|---|---|---|---|---|---|---|
| 1 | PEGDA | 0.80 | 575 | DEA | 1.61 | 1 | 90 |
| 2 | TMP(EO)TA | 0.48 | 912 | DEA | 2.43 | 1 | 90 |
| 3 | PEGDA | 0.48 | 575 | DEA | 1.91 | 1 | 90 |
| 4 | PEGDA | 0.280 | 575 | DEA | 0.559 | 1 | 100 |
| 5 | HDDA | 0.414 | NP | DEA | 0.828 | 1.5 | 80 |
| 6 | TMP(EO)TA | 1.39 | 956 | DEA | 5.56 | 4 | 120 |
| 7 | TMP(EO)TA | 1.69 | 956 | DEA | 5.25 | 1 | 90 |
| 8 | TMP(EO)TA | 1.95 | 956 | DEA | 5.87 | 4 | 110 |
| 9 | TMP(EO)TA | 0.487 | 912 | DEA | 1.46 | 4 | 110 |
| 10 | TMP(EO)TA | 0.214 | 912 | DEA | 0.641 | 1 | 80 |
| 11 | TMP(EO)TA | 0.496 | 912 | DEA | 1.47 | 2 | 80 |
| 12 | DPGDA | 0.251 | NP | DPA | 0.502 | 19 | 20 |
| 13 | P(PG)DA | 0.562 | 900 | DEA | 1.12 | 2 | 100 |
| 14 | DEGDA | 0.391 | NP | DEA | 0.989 | 1 | 80 |
| 15 | TMPTA | 0.287 | NP | DEA | 0.862 | 1 | 100 |
| 16 | TMP(EO)TA | 0.80 | 912 | DEA | 2.93 | 1 | 90 |
| 17 | TMP(EO)TA | 0.80 | 912 | DEA | 7.30 | 1 | 90 |
| 18 | PETA | 0.287 | NP | DEA | 1.15 | 1 | 100 |
| 19 | diTMPPMA | 0.80 | NP | DEA | ~3 | 1 | 90 |
| 20 | HEMA | 0.280 | | DEA | 0.559 | 1 | 100 |

NP = non polymeric so $M_n$ is molecular weight of compound

TABLE 1b (data to 3sf)

| Ex | Solvent (SOL) | f SOL (g) | g MP (ppm) | h PT (ppm) | i NB (ppm) | j TNPP (ppm) | ACR2 |
|---|---|---|---|---|---|---|---|
| 1 | TOL | 260 | 625 | 625 | 400 | 500 | AA |
| 2 | TOL | 351 | 625 | 625 | 400 | 500 | AA |
| 3 | TOL | 351 | 625 | 625 | 400 | 500 | AA |
| 4 | TOL | 200 | 2500 | — | 400 | — | AA |
| 5 | TOL | 250 | 2500 | 2500 | 400 | — | AA |
| 6 | NPA | 751 | 1250 | 1250 | 2000 | 500 | AA |
| 7 | — | — | 625 | 625 | 1000 | 500 | AA |
| 8 | PEN | 605 | 1250 | 1250 | 2000 | 500 | AA |
| 9 | IPA | 249 | 1500 | 1500 | 1500 | 500 | AA |
| 10 | MCH | 100 | 625 | 625 | 400 | 500 | AA |
| 11 | MCH | 200 | 1000 (*TBHQ) | 625 | 1000 | 500 | AA |
| 12 | TOL | 200 | 2500 | — | 400 | — | AA |
| 13 | MCH | 400 | 625 | 625 | 400 | 500 | AA |
| 14 | TOL | 200 | 2500 | — | 400 | — | AA |
| 15 | TOL | 100 | 2500 | — | 400 | — | AA |
| 16 | TOL | 351 | 625 | 625 | 400 | 500 | MA |
| 17 | TOL | 351 | 625 | 625 | 400 | 500 | AA |
| 18 | TOL | 100 | 2500 | — | 400 | — | AA |
| 19 | TOL | 351 | 625 | 625 | 400 | 500 | AA |
| 20 | TOL | 200 | 625 | 625 | 400 | 500 | AA |

TABLE 1c (data to 3sf)

| Ex | k (mol) | l MP ppm | m PT ppm | p hr | q mbar | n' | x' + y' + z' | r |
|---|---|---|---|---|---|---|---|---|
| 1 | 4.65 | 625 | 625 | 20 | 7 | ~10 | — | liq |
| 2 | 4.0 | 625 | 625 | 20 | 7 | — | ~14 | liq |

TABLE 1c-continued (data to 3sf)

| Ex | k (mol) | l MP ppm | m PT ppm | p hr | q mbar | n' | x' + y' + z' | r |
|---|---|---|---|---|---|---|---|---|
| 3 | 5.53 | 625 | 625 | 20 | 7 | ~10 | — | liq |
| 4 | 2.24 | — | — | 21 | 7 | ~10 | — | liq |
| 5 | 2.73 | — | — | 16 | 8 | — | — | liq |
| 6 | 15.0 | — | — | 21 | 10 | — | ~15 | liq |
| 7 | 25.4 | 625 | 625 | | 5 | — | ~15 | liq |
| 8 | 14.1 | — | — | 21 | 6 | — | ~14 | liq |
| 9 | 3.51 | — | — | 24 | 8 | — | ~14 | liq |
| 10 | 3.51 | 625 | 625 | 20 | 8 | — | ~14 | liq |
| 11 | 4.31 | 1000 (*TBHQ) | 625 | 20 | 10 | — | ~14 | liq |
| 12 | 1.10 | — | — | 22 | 3 | — | — | liq |
| 13 | 4.31 | 625 | 625 | 20 | 8 | ~13 | — | liq |
| 14 | 3.13 | — | — | 8 | 8 | — | — | liq |
| 15 | 3.45 | — | — | 21 | 2 | — | — | liq |
| 16 | 4.0 | 625 | 625 | 20 | 2 | 1 | ~14 | MN |
| 17 | 21.6 | — | — | 20 | 2 | 1 | ~20 | MN |
| 18 | 3.45 | — | — | 21 | 2 | — | — | MN |
| 19 | 4.31 | 625 | 625 | 20 | 2 | 1 | — | MN |
| 20 | 5.53 | 625 | 625 | 21 | 7 | ~10 | — | MN |

NM denotes not measured

TABLE 1d (data to 3sf)

| Ex | s mPas | t rpm | u (nbr Ac) | v (% conv) | w (max Ac) |
|---|---|---|---|---|---|
| 1 | 707 | 60 | 4.0 | 100 | 4 |
| 2 | 1350 | 30 | 5.5 | 92 | 6 |
| 3 | 1960 | 20 | 5.6 | 100 | 6 |
| 4 | 755 | 60 | 3.6 | 90 | 4 |
| 5 | 745 | 60 | 3.8 | 95 | 4 |
| 6 | 1980 | 20 | 6.4 | 92 | 7 |
| 7 | 2720 | 12 | 6.0 | 100 | 6 |
| 8 | NM | — | 3.54 | 59 | 6 |
| 9 | NM | — | 3.84 | 64 | 6 |
| 10 | 1210 | 30 | 4.0 | 80 | 5 |
| 11 | 1400 | 30 | 5.0 | 83 | 6 |
| 12 | 6400 | 6 | 3.8 | 95 | 4 |
| 13 | NM | NM | NM | NM | 4 |
| 14 | 3800 | 12 | 3.3 | 73 | 4.5 |
| 15 | 12400 | 4 | 5.7 | 95 | 6 |
| 16 | MN | NM | NM | NM | NM |
| 17 | MN | NM | NM | NM | NM |
| 18 | MN | NM | NM | NM | NM |
| 19 | MN | NM | NM | NM | NM |
| 20 | MN | NM | NM | NM | NM |

NM denotes not measured

Example 1

Macromolecules presumably represented by the average structure Formula 1 are prepared by the standard method with reference to Table 1.

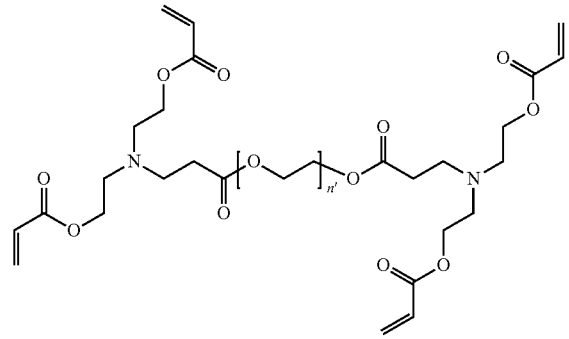

Formula 1

Example 2

Macromolecules presumably represented by the average structure Formula 2 are prepared by the standard method with reference to Table 1.

Formula 2

Example 3

Macromolecules presumably represented by the average structure Formula 3 are prepared by the standard method with reference to Table 1.

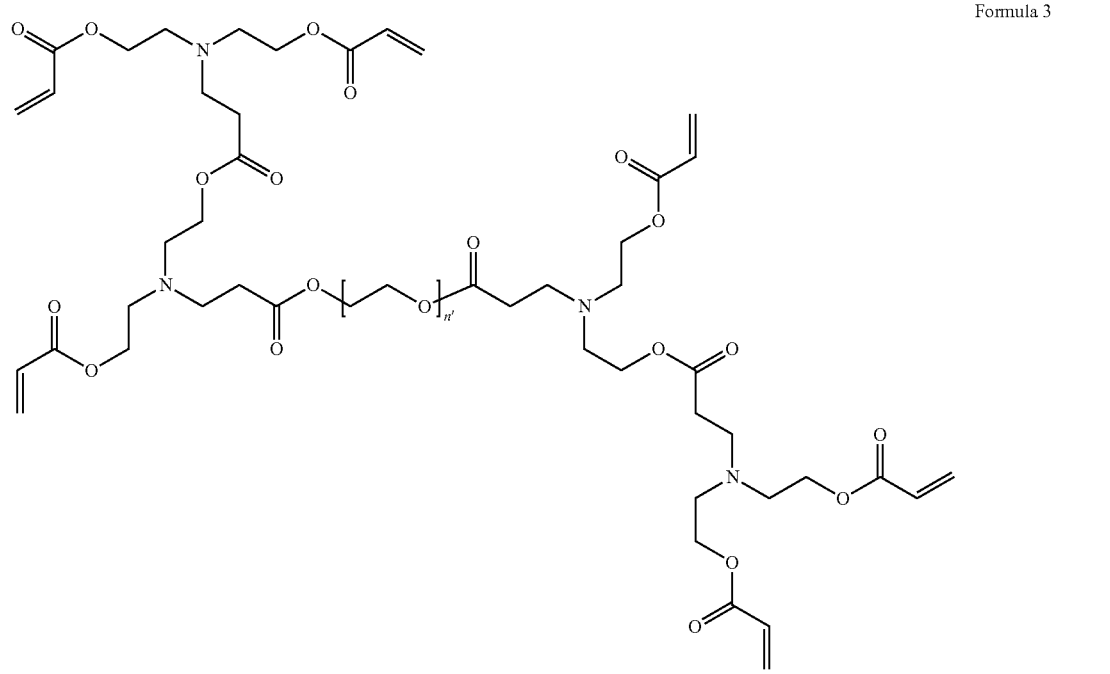

Formula 3

Example 4

Macromolecules presumably represented by the average structure Formula 1 (as given in Example 1) are prepared by the standard method with reference to Table 1, except that the second acrylate (ACY2) and solvent (SOL) are added simultaneously with the radical stabilisers after $^1$H-NMR shows that all acrylate groups have reacted in the previous step.

A considerable reduction in the viscosity of the product is achieved by diluting with small amounts of water as shown below.

| Ex | Viscosity (measured at 100 rpm) | Weight % of water added |
| --- | --- | --- |
| 4a | 422 mPa.s | 5 % |
| 4b | 275 mPa.s | 10 % |
| 4c | 204 mPa.s | 15 % |

Clear films can be made from the pure product and from the diluted product. Adhesion properties of such films are excellent (0% lift off) for 7 out of 12 tests and good for another 2 out of 12 tests (as above) with the undiluted product. For a film made with Composition 5b adhesion properties were excellent for 10 out of 12 tests and good for another 1 out of 12.

Example 5

Macromolecules presumably represented by the average structure Formula 5 are prepared by the standard method with reference to Table 1, except that the second acrylate (ACY2) and solvent (SOL) are added simultaneously with the radical stabilisers after $^1$H-NMR shows that all acrylate groups have reacted in the previous step.

Formula 5

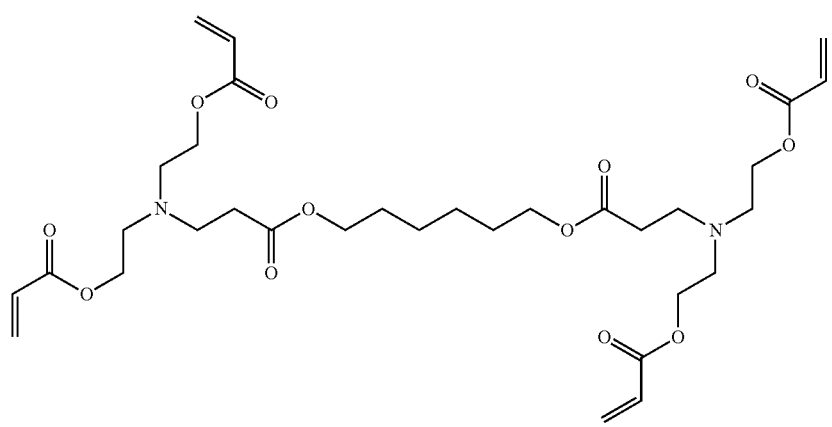

Example 6

Macromolecules presumably represented by the average structure Formula 6 are prepared by the standard method with reference to Table 1, except that the amine (AM(OH)) was added under reduced pressure and under nitrogen and the mixture is then cooled to 110° C. and then the second acrylate (ACY2) and solvent (SOL) are added simultaneously with the radical stabilisers. The solvent was removed from the final mixture at by distillation under reduced pressure at a temperature of 125° C.

Formula 6

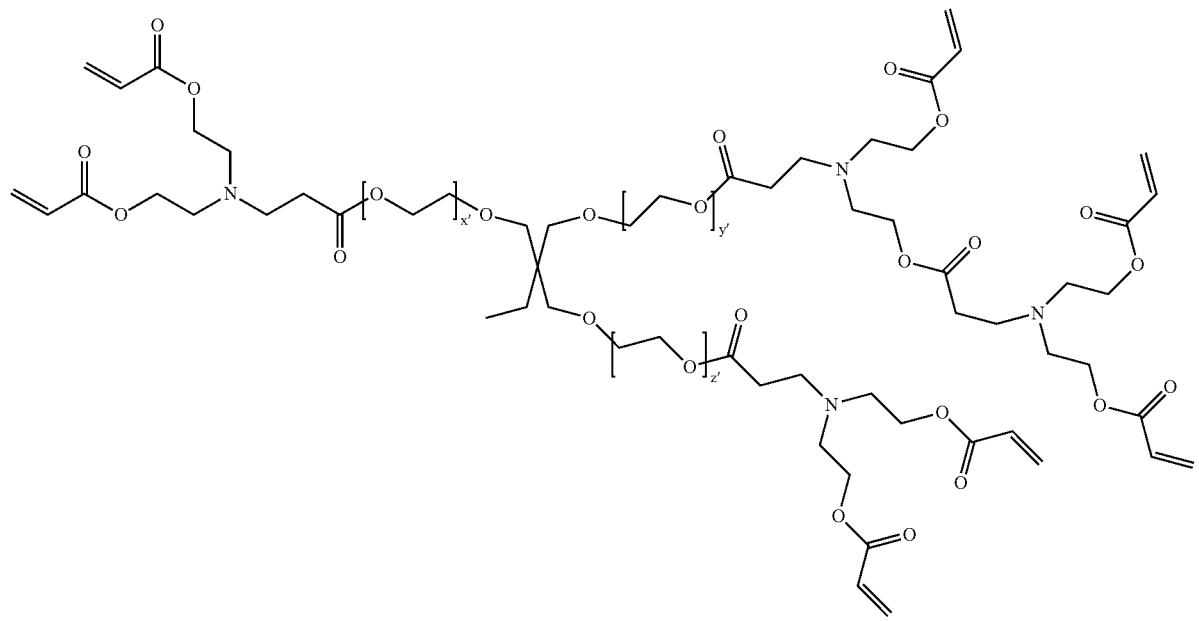

Example 7

Macromolecules presumably represented by the average structure Formula 7 are prepared by the standard method with reference to Table 1, except that TNPP and a first amount of NB stabilisers are added to the reaction mixture 1.5 hours after the MP and PT stabilisers to form an intermediate of acid value 364 mg/mg KOH, when mixture is heated till 100° C. and kept at this temperature for 4 hours and the further NB is added so after 2 hours the acid value of the mixture drops to 209 mg/mg KOH. The solvent is removed from the final mixture at by distillation under reduced pressure at a temperature of 125° C. to obtain a product of acid value 34 mg/mg KOH.

Example 8

Macromolecules presumably represented by the average structure Formula 7 (in Example 7) are prepared by the standard method with reference to Table 1, except that the amine (AM(OH)) was added under reduced pressure and under nitrogen and the mixture is then cooled to 80° C. and then the second acrylate (ACY2) and solvent (SOL) are added simultaneously with the radical stabilisers. The solvent was removed from the final mixture at by distillation under reduced pressure at a temperature of 125° C.

Example 9

Macromolecules presumably represented by the average structure Formula 2 (in Example 2) are prepared by the standard method with reference to Table 1, except that the amine (AM(OH)) was added under reduced pressure and under nitrogen and the mixture is then cooled to 95° C. and then the second acrylate (ACY2) and solvent (SOL) are added simultaneously with the radical stabilisers. The solvent was removed from the final mixture at by distillation under reduced pressure at a temperature of 124° C.

Example 10

Macromolecules presumably represented by the average structure of Formula 10 are prepared by the standard method with reference to Table 1, except that one hour after the first acrylate (ACR1) and the amine (AM(OH)) have begun to react then 0.2138 mol of lauric acid is added and the reaction mixture which is then heated till 170° C. under nitrogen. After 45 minutes water formed during the reaction is removed under reduced pressure (5 mbar). After a further 4 hours the mixture has an acid value of 1.8 mg/mg KOH and is cooled to 60° C. and then the remaining steps of the standard method (with reference to Table 1) are followed.

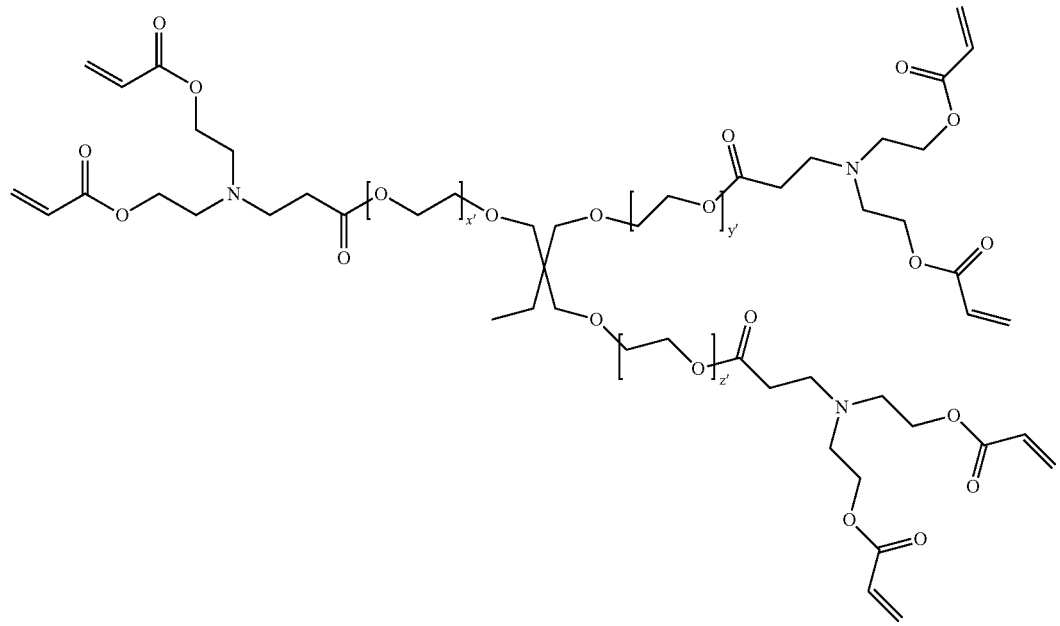

Formula 7

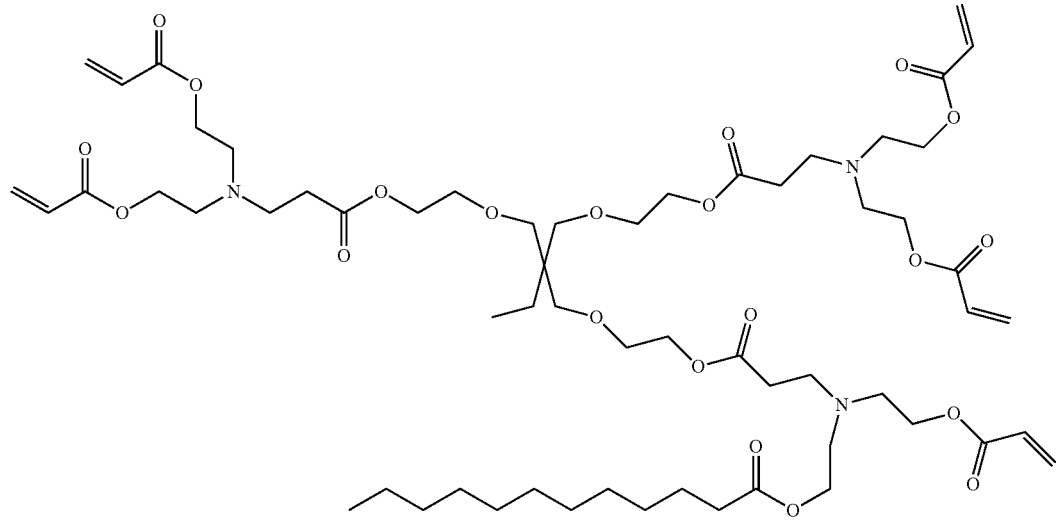

Formula 10

Example 11

Macromolecules presumably represented by the average structure Formula 2 (in Example 2) are prepared by the standard method with reference to Table 1, except the methoxy phenol (MP) stabiliser is replaced by tertiary butyl hydroquinone (TBHQ).

Example 12

Macromolecules presumably represented by the average structure Formula 12 are prepared by the standard method with reference to Table 1

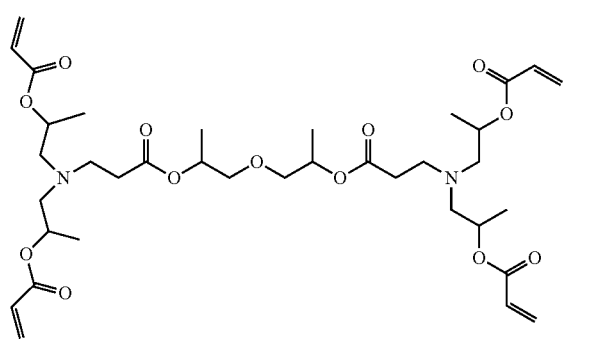

Formula 12

Example 13

Macromolecules presumably represented by the average structure Formula 13 are prepared by the standard method with reference to Table 1.

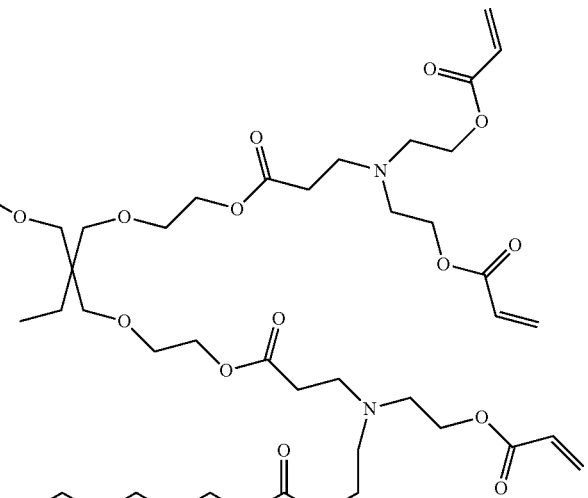

Formula 13

Example 14

Macromolecules of presumed structures Formulae 14a and 14b are prepared by the standard method with reference to Table 1, where 'w' the maximum acrylic value (4.5) is the mean of the mixture of macromolecules that comprise the example.

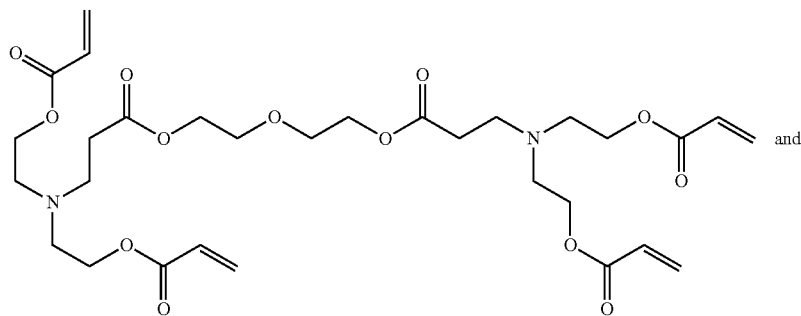

Formula 14a

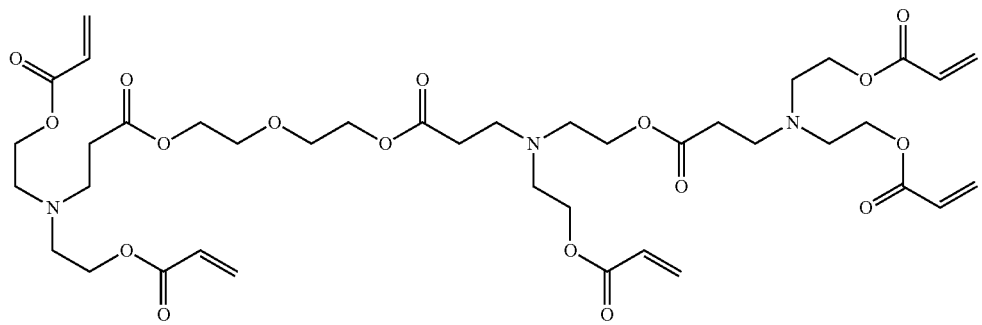

Formula 14b

Example 15

Macromolecules of presumed structure Formula 15 are prepared by the standard method with reference to Table 1.

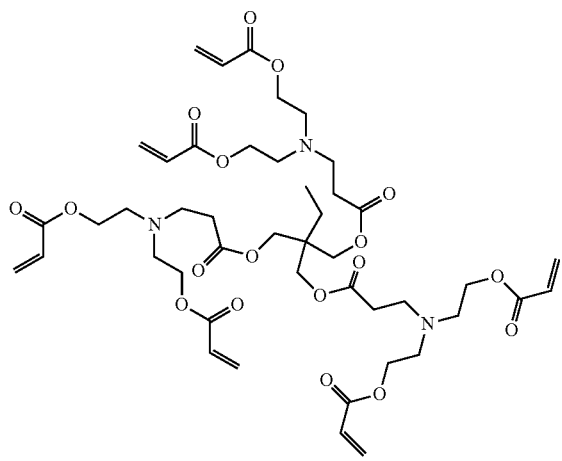

Formula 15

Examples 16 to 20

Other macromolecules may be prepared according the present invention using the Standard Method and the parameters given in Tables 1a, 1b and 1c.

Example 17 is a product where the hydroxy amine ('c' mol) and (acrylic) acid ('k' mol) are present in sufficiently large excess so that after esterification for the first time in step (b) the resultant acrylate ester undergoes further Michael addition with amine forming a further adduct which is further esterified with the acid (i.e. steps (a) and (b) occur twice).

Other larger macromolecules of the invention can be produced similarly, optionally using different amines and acids using two or more repetitions of steps (a) and (b).

Example A to E

Formulations and Films

Many formulations can be made using any of the macromolecules exemplified herein. The formulations can be coated onto suitable substrates and their properties measured to illustrate the advantages of the present invention.

As non-limiting representative examples, formulations are made comprising macromolecules of Example 1, 2 or 3, all figures given as weight % of the total formulation (to 3sf).

TABLE 2

| Example (formulation) | A | B | C | D | E |
|---|---|---|---|---|---|
| Ex 1 (from PEGDA) | 47.3 | — | — | — | — |
| Ex 2 (from TMP(EO)TA) | — | 47.3 | 42.3 | — | — |
| Ex 3 (from PEGDA) | — | — | — | 47.3 | 42.3 |
| H$_2$O | — | — | 5 | — | 5 |
| Benzophenone | 2.5 | 2.5 | 2.5 | 2.5 | 2.5 |
| MDEA | | | | | |
| Anti-crater agent | 0.25 | 0.25 | 0.5 | 0.25 | 0.5 |
| Total | 50 | 50 | 50 | 50 | 50 |

Due to rounding the data may not total 100%.

In formulations C and E 10 wt. % water is added to show the macromolecules are well dilutable with water.

Film Testing

From each of the formulations A to E above 6 μm thick, clear films are cast in a conventional manner. The films are cured by irradiating at 200, 400 or 600 J/cm$^2$ using an H-bulb (mercury bulb). The relative curing speed of these formulations can be assessed indirectly from the gloss of the cured film after being subject to 50 double rubs (in a standard protocol) of a methyl ethyl ketone (MEK) solvent. Higher gloss ratings result from films more resistant to MEK i.e. where the formulation undergoes a more complete cure for a given radiation dose. Thus the higher gloss rating the better the cure speed. The gloss is assessed visually with respect to gloss card reference and then given a value in the following table from 0 to 5, where 5 is excellent and 0 is poor. The data shows that excellent curing speed is achieved at energies of 600 J/cm² or less.

TABLE 3

| Radiation dose | A | B | C | D | E |
|---|---|---|---|---|---|
| 200 mJ/cm² | 4 | 3 | 3 | 5 | 4 |
| 400 mJ/cm² | 5 | 5 | 4 | — | 5 |
| 600 mJ/cm² | — | — | 5 | — | — |

The gloss of the cured coating is assessed using test method DIN 67530, with a micro-Trigloss apparatus from Byk Gardnes taking an average of three measurements. The gloss is acceptable for each of the formulations, although undiluted formulations have better gloss (73 to 76) at 20° than diluted ones (53 to 63) All formulations shrink very little on curing at 600 J/cm² (each is given a shrink rating of 4.5 out of 5.)

The König hardness after curing at 600 J/cm² is determined for a 24 µm thick film made from each of the formulations A to E. The results are as follows:

TABLE 4

|  | A | B | C | D | E |
|---|---|---|---|---|---|
| König hardness (sec.) (Glass) * | 62 | 83 | 71 | 52 | 44 |

The hardness is acceptable for all formulations. The cured films made from the formulations without water (B and D) have a higher hardness than those films made from formulations that contain water (C and E).

Adhesion of the cured film (thickness 12 µm) to various substrates is tested using three commercially available tapes (Sello 25 mm, Scotch 20 mm, and Scapa). In this test an ink comprising a curable composition of the invention is applied to a plastic substrate by means of a squeegee (12 µm). A reference ink (with known adhesion to the substrate) is applied adjacent to the test ink on the same substrate at the same time in the same manner. The inked substrate is then dried in an oven for 10 sec at 80° C. After cooling, a strip of the tape is placed to completely cover the dried ink and is pressed very firmly by hand to remove any air bubbles. The tape is removed by hand and the ink remaining on the substrate is visually assessed and the percentage of ink removed is recorded (0% being best, 100% indicating no adhesion). The lower the percentage the better an ink adheres to a substrate.

Comp Z is a reference ink. It is prepared in a similar manner to the test inks as described herein except the macromolecule Examples in formulations A to E were replaced by a conventional polyester acrylate having an average of four acrylate groups per molecule and a $M_n$ of about 850 g/mol (available commercially from DSM under the trade mark Neorad P20).

Comp Z poorly adhered to these substrates as it was nearly completely removed in these tests whereas formulations A to E of the invention show excellent adhesion.

TABLE 5

|  | A | B | C | D | E | Comp Z |
|---|---|---|---|---|---|---|
| Adhesion on, MEL S (% lift off) | | | | | | |
| Sello | 0 | 0 | 0 | 0 | 0 | 100 |
| Scotch | 0 | 0 | 0 | 0 | 0 | 100 |
| Scapa | 0 | 0 | 0 | 0 | 0 | 100 |
| Adhesion on coex OPP, MB 400 (% lift off) | | | | | | |
| Sello | 0 | 0 | 0 | 0 | 0 | 90 |
| Scotch | 0 | 0 | 0 | 0 | 10 | 0 |
| Scapa | 0 | 0 | 0 | 0 | 0 | 100 |
| Adhesion on PET, Melinex 813 (% lift off) | | | | | | |
| Sello | 0 | 0 | 0 | 0 | 0 | 100 |
| Scotch | 0 | 0 | 0 | 0 | 0 | 100 |
| Scapa | 0 | 0 | 0 | 0 | 0 | 100 |
| Adhesion on PVC, filmtex (% lift off) | | | | | | |
| Sello | 0 | 0 | 0 | 0 | 0 | 10 |
| Scotch | 0 | 0 | 0 | 0 | 0 | 0 |
| Scapa | 0 | 0 | 0 | 0 | 0 | 50 |

The other examples herein may be similarly formulated (for example using conventional ink pastes). The cured coatings may be tested to show similar or advantageous properties to prior art inks. Thus use of macromolecules of the invention provides reactive diluents with improved properties and the final ink has properties comparable to known inks.

TABLE 6

(paste and ink formulations)
(all figures mass in g unless otherwise stated)

| | | | | | | | L |
| | | | | I | J | K | Ex G + |
| | F | G | H | (Ex G) | (Ex G) | (Ex G) | 20% water |
|---|---|---|---|---|---|---|---|
| Paste pre grinded with dissolver | | | | | | | |
| Neorad P20 | 83.6 | — | — | — | — | — | — |
| U70 | 24.8 | — | — | — | — | — | — |
| Example 11 | — | 108.4 | — | 16.3 | 16.3 | 16.3 | 108.4 |
| Example 3 | — | — | 108.4 | — | — | — | — |
| Solsperse 5000 | 0.9 | 0.9 | 0.9 | — | — | — | 0.9 |

TABLE 6-continued (paste and ink formulations)
(all figures mass in g unless otherwise stated)

| | | | | Example | | | |
|---|---|---|---|---|---|---|---|
| | F | G | H | I (Ex G) | J (Ex G) | K (Ex G) | L Ex G + 20% water |
| Solsperse 32000 | 2.9 | 2.9 | 2.9 | — | — | — | 2.9 |
| Irgalite blue GLO | 37.9 | 37.9 | 37.9 | — | — | — | 37.9 |
| total | 150 | 150 | 150 | 16.3 | 16.3 | 16.3 | 150 |
| | | | Ink: | | | | |
| Paste | 22.5 | 22.5 | 22.5 | — | — | — | 25 |
| Water | — | — | — | — | — | — | 5 |
| MEK | — | — | — | — | — | 6.2 | — |
| HDDA | 3.6 | 3.6 | 3.6 | 3.6 | 3.6 | 3.6 | 2.5 |
| TPGDA | 11.7 | 11.7 | 11.7 | 11.7 | 11.7 | 11.7 | 8.9 |
| TMPTA | 8.6 | 8.6 | 8.6 | 8.6 | 8.6 | 8.6 | 6.4 |
| MDEA | 0.8 | 0.8 | 0.8 | 0.8 | — | 0.8 | — |
| Darocure TPO* | 0.9 | 0.9 | 0.9 | 0.9 | 0.9 | 0.9 | 0.7 |
| Irgacure 379* | 0.9 | 0.9 | 0.9 | 0.9 | 0.9 | 0.9 | 0.7 |
| Darocure BP* | 1 | 1 | 1 | 1 | 1 | 1 | 0.7 |
| total | 50 | 50 | 50 | 43.8 | 43 | 50 | 50 |
| Viscosity (mPas) | 3100 | 2460 | 1570 | — | — | — | — |
| % pigment | 11.4 | 11.4 | 11.4 | 0 | 0 | 0 | 12.6 |

Those asterisked ingredients are conventional photo-initiators available commercially under the trade names given in the table. U70 is a conventional polyurethane ingredient for ink formulations available commercially from DSM under this trade designation. In formulations I and J the pigment (Irgalite blue GLO) and dispersing agents (Solsperse 5000 or 32000) (available commercially under these trade names) are omitted without correcting for their volume. In formulation K the volume is adjusted by adding MEK. These formulations may be cured at a cure speed of 1200 mJ/cm$^2$ to produce coatings with the following properties (Table 7).

TABLE 7

| | Ex G | Ex H | Ex I |
|---|---|---|---|
| Viscosity (mPa.s) | 3100 | 2760 | 1740 |
| Transparency (transparency card,12μm) | 2 | 3 | 3-4 |
| Grains (PET, 12μm) | 5 | 5 | 5 |
| Satra rub (Leneta transparency card, 12μm) | | | |
| 4000 Dry | 4 | 4 | 4-5 |
| 4000 olive oil | 3 | 3 | 4 |
| Gloss (Gloss-card, 12μm) | | | |
| 20° | 10 | 39 | 62 |
| 60° | 78 | 84 | 85 |
| Shrink (Gloss-card, 12μm) | | | |
| | 5 | 5 | 5 |
| Double MEK rubs (Gloss-card, 12μm) | | | |
| 200 | 5 | 5 | 5 |
| König Hardness (sec) | | | |
| 24μm @ 1200mJ/cm$^2$ | 54 | 35 | 28 |

The adhesion of these coatings to various substrates was also tested and is given in Table 8, where Comp Y is a conventional UV curable ink. Ink formulations of the invention show comparable or improved adhesion to conventional inks on a variety of substrates.

TABLE 8

| | Ex | | | | |
|---|---|---|---|---|---|
| | I | J | K | L | Comp Y |
| Adhesion on, OPP CoEx MB 200 (% lift off) | | | | | |
| Sello | 0 | 0 | 20 | 0 | 0 |
| Adhesion on coex OPP, XL 210 (% lift off) | | | | | |
| Scotch | 0 | 0 | 0 | 0 | 100 |
| Sello | 0 | 0 | 0 | 0 | 0 |
| Adhesion on PVC, ex Fasson (% lift off) | | | | | |
| Scotch | 0 | 0 | 0 | 0 | 0 |
| Sello | 0 | 0 | 0 | 0 | 0 |
| Scapa | 0 | 0 | 0 | 0 | 0 |
| Adhesion on PE, ex Oerlemans (% lift off) | | | | | |
| Scotch | 0 | 0 | 0 | 0 | 5 |
| Sello | 0 | 0 | 0 | 0 | 20 |

The invention claimed is:

1. A method for preparing a branched non-dendrimeric macromolecule, the method comprising the steps of:
    a) providing an addition product of an α,β-olefinically unsaturated compound and an amine comprising at least two hydroxyl groups; and
    b) esterifying at least part of the hydroxyl groups of the addition product with an olefinically unsaturated compound selected from the group consisting of an olefinically unsaturated carboxylic acid, an olefinically unsaturated carboxylate, an olefinically unsaturated carboxylic acid anhydride, an ester of an olefinically unsaturated carboxylic acid, and an olefinically unsaturated acid halogenide to obtain an esterified compound of the addition product.

2. The method according to claim 1, wherein step a) comprises subjecting the α,β-olefinically unsaturated compound and an amine comprising at least two hydroxyl groups to an addition reaction, and wherein step b) comprises subjecting the esterified compound of the addition product to the addition reaction of step a).

3. The method according to claim 2, further comprising esterifying or etherifying at least part of the hydroxyl groups of the addition product according to step b).

4. The method according to claim 3, wherein the esterification comprises carrying out an esterification reaction according to step b).

5. The method according to claim 3, wherein the esterification or etherification comprises reacting the hydroxyl group with a fatty acid, a fatty acid anhydride, a polyalkoxylate or a polyalkoxy-anhydride.

6. The method according to claim 1, wherein the addition product is provided by reacting the amine in a stoichiomeric excess with respect to the number of olefinic unsaturations in said α,β-olefinically unsaturated compound.

7. The method according to claim 1, wherein the number of olefinic unsaturations in the branched macromolecular compound is larger than in said α,β-olefinically unsaturated ester.

8. The method according to claim 1, wherein the olefinically unsaturated compound is represented by Formula IX

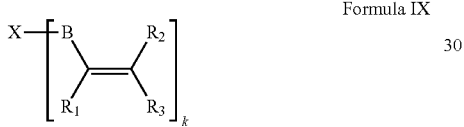

Formula IX where
X is silanol based moiety or an organic moiety, which optionally comprises one or more heteroatoms and which optionally comprises one or more substituents;
B is selected from the group consisting of carbonyloxy, oxy carbonyl and oxy groups;
$R_1$, $R_2$, and $R_3$ are each independently selected from the group comprising hydrogen and hydrocarbo moieties, including hydrocarbo moieties additionally comprising one or more heteroatoms and hydrocarbo moieties comprising substituents, preferably of the group of hydrogen and alkyl moieties, including substituted alkyl moieties; and
k is an integer having a value of at least 1, in particular of 1-20.

9. The method according to claim 1, wherein the amine is represented by the formula $R^x$—NH—$R^y$, wherein $R^x$ and $R^y$ are independently selected from the group of hydroxy-alkyl moieties and polyetherol moieties, preferably from hydroxyethyl, hydroxypropyl, polyethylene oxide and polypropylene oxide.

10. A non-dendrimeric branched macromolecule obtained by a method according to claim 1.

11. A non-dendrimeric macromolecule represented by Formula I:

Formula I where
X is an organo, silcio or organo-silico moiety,
n is 0 or an integer of at least 1, m is an integer of at least 1; and the sum of n and m (also referred to herein as "k") is ≧1,
Y is represented by Formula II:

Formula II where
$R_1$, $R_2$ and $R_3$ are each independently selected from the group of hydrogen and hydrocarbo moieties; and
B represents a moiety selected from the group consisting of: carbonyloxy [—(C=O)O—], oxycarbonyl [—O(C=O)—] and oxy [—O—]; and
Z is represented by Formula III:

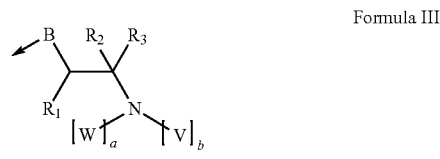

Formula III where
B, $R_1$, $R_2$ and $R_3$ are each independently as defined for Formula II;
a is 0 or 1, b is 1, 2 or 3, and the sum of a and b (also referred to herein as "c") is 2 or 3,
W is hydrogen, alkyl or V; and
V is each independently represented by one of Formulae IV to VI:

Formula IV

Formula V

Formula VI where
$R_4$, $R_5$, $R_6$, $R_8$, $R_9$, and $R_{10}$ are each independently organo groups;
U is each independently selected from the group consisting of: hydroxy, carbonyl-$R_{11}$ [—(C=O)$R_{11}$] and moieties represented by Formulae VII and VIII:

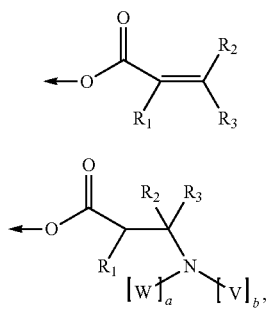

Formula VII

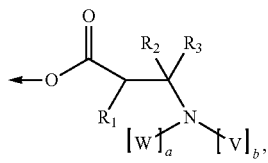

Formula VIII where:

V, W, $R_1$, $R_2$, $R_3$, a and b are each independently as defined for Formulae II and III; and $R_{11}$ is an organo group.

12. A branched macromolecule according to claim 10, comprising at least 1 olefinically unsaturated polymerisable group.

13. The branched macromolecule according to claim 10, having a Brookfield viscosity at 25° C. of up to 10 Pa·s.

14. A coating composition comprising non-dendrimeric macromolecules according to claim 10, and one or more additives selected from the group consisting of diluents, pigments, dyes, flow agents, levelling agents, anticrater-agents, initiators, adhesion modifiers, viscosity modifiers, tackifiers, waxes, dispersants, synergists, wetting agents, silicones, slip additives, anti-block agents, surface tension reducing agents, fillers, matting agents, adhesion promoters, rheology modifiers, UV-stabilisers, defoamers, thickeners, and other polymers.

15. Ink, toner or varnish comprising non-dendrimeric macromolecules according to claim 10, and one or more additives selected from the group consisting of diluents, pigments, dyes, flow agents, levelling agents, (further) polymers, fillers, initiators, synergists, UV stabilisers, pigment wetting agents, dispersants, defoamers, rheology modifiers, thickeners, adhesion promoters, matting agents, tackifiers, waxes, slip additives and anti-block agents.

16. An adhesive comprising non-dendrimeric macromolecules according to claim 10, and one or more additives selected from the group consisting of diluents pigments, dyes, flow agents, levelling agents, anticrater-agents, initiators, adhesion modifiers, viscosity modifiers, tackifiers, wax, dispersants, synergists, wetting agents, silicones, slip additives, anti-block agents, surface tension reducing agents, fillers, matting agents, adhesion promoters, rheology modifiers, UV-stabilisers, defoamers, thickeners, and polymers.

17. A curable composition comprising non-dendrimeric macromolecules according to claim 10 having curable olefinically unsaturated groups and at least one further curable compound comprising curable groups different from olefinically unsaturated groups.

18. A sprayable composition comprising non-dendrimeric macromolecules according to claim 10.

19. A polymer comprising non-dendrimeric macromolecules according to claim 10, and optionally one or more other polymerisable compounds.

20. A coated substrate comprising a substrate and a coating on the substrate, wherein the coating is comprised of a coating composition according to claim 14.

21. A radiation curable composition comprising:
   a) from 1 to 99% by weight of radiation curable monomers;
   b) from 1 to 99% by weight of non-dendrimeric macromolecules according to claim 10,
   c) optionally from 0 to 10% of one or more photo-initiators, wherein
   the weight percentages are calculated from the total of a), b) and c) which total 100%.

22. The radiation curable composition of claim 21, wherein the composition exhibits at least one of the following properties:
   i) low shrink on curing, preferably less than 10% shrink;
   ii) high speed cure, preferably being substantially cured after irradiation at an energy of 600 mJcm$^{-2}$; and/or
   iii) low viscosity, preferably less than 10 mPa·s.

23. The radiation curable composition of claim 21, wherein the composition is curable by UV radiation.

24. The branched macromolecule of claim 12, comprising at least 2 olefinically unsaturated polymerisable groups.

25. The branched macromolecule of claim 12, comprising from 4 to 16 olefinically unsaturated polymerisable groups.

26. The branched macromolecule according to claim 10, having a Brookfield viscosity at 25° C. of from 0.3 to 2 Pa·s.

* * * * *